(12) United States Patent
Marinelli et al.

(10) Patent No.: US 9,452,089 B2
(45) Date of Patent: *Sep. 27, 2016

(54) METHODS OF MAKING ABSORBENT MEMBERS HAVING DENSITY PROFILE

(75) Inventors: Luigi Marinelli, Pescara (IT); Kirk Wallace Lake, Cincinnati, OH (US); Jill Marlene Orr, Liberty, OH (US); John Brian Strube, Okeana, OH (US); Keith Robert Priessman, Hamilton, OH (US); Carmine Cimini, Pescara (IT); Mario Dipilla, Pescara (IT)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/455,194

(22) Filed: Apr. 25, 2012

(65) Prior Publication Data

US 2012/0277710 A1    Nov. 1, 2012

Related U.S. Application Data

(63) Continuation-in-part of application No. 13/094,295, filed on Apr. 26, 2011.

(51) Int. Cl.
*B31F 1/00* (2006.01)
*A61F 13/15* (2006.01)
(Continued)

(52) U.S. Cl.
CPC ... *A61F 13/15731* (2013.01); *A61F 13/15617* (2013.01); *B26F 1/20* (2013.01);
(Continued)

(58) Field of Classification Search
CPC .................. A61F 13/15626; A61F 13/15731; A61F 2013/15439; B31F 2201/0774; D21H 27/007

USPC ........ 162/204, 205, 206, 361, 362; 264/284, 264/285

See application file for complete search history.

(56) References Cited

U.S. PATENT DOCUMENTS

| 3,017,304 A | 1/1962 | Burgeni |
| 3,496,259 A | 2/1970 | Guenther |

(Continued)

FOREIGN PATENT DOCUMENTS

| DE | 4024053 A1 | 1/1992 |
| EP | 0598970 A1 | 6/1994 |

(Continued)

OTHER PUBLICATIONS

U.S. Appl. No. 13/094,477, filed Apr. 26, 2011, Keith Joseph Stone et al.

(Continued)

*Primary Examiner* — Galen Hauth
(74) *Attorney, Agent, or Firm* — Jeffrey V Bamber

(57) ABSTRACT

Absorbent members and methods of making the same are disclosed. In one embodiment, the absorbent member is a unitary absorbent fibrous web having a density profile through its thickness. In one embodiment, the density profile is relatively centered through the thickness of the web and the maximum density of the web is located between about 35% and about 65% of the distance through the thickness of the web. In one embodiment, the method involves subjecting a precursor web to at least one cycle (or pass) through a mechanical deformation process. Typically, the method involves subjecting the precursor web to multiples cycles (or passes) through a mechanical deformation process.

39 Claims, 19 Drawing Sheets

(51) Int. Cl.
  *B31F 1/07* (2006.01)
  *B26F 1/20* (2006.01)
  *B26F 1/24* (2006.01)
(52) U.S. Cl.
  CPC .................. *B26F 1/24* (2013.01); *B31F 1/07*
    (2013.01); *A61F 2013/15439* (2013.01); *B31F*
    *2201/0774* (2013.01)

(56) References Cited

U.S. PATENT DOCUMENTS

| | | | |
|---|---|---|---|
| 3,509,007 | A | 4/1970 | Kalwaites |
| 3,994,771 | A | 11/1976 | Morgan, Jr. et al. |
| 4,189,344 | A | 2/1980 | Busker |
| 4,300,981 | A | 11/1981 | Carstens |
| 4,761,322 | A | 8/1988 | Raley |
| 4,992,324 | A | 2/1991 | Dube |
| 5,143,679 | A | 9/1992 | Weber et al. |
| 5,167,897 | A * | 12/1992 | Weber et al. ............. 264/288.8 |
| 5,217,445 | A * | 6/1993 | Young et al. ............... 604/381 |
| 5,242,435 | A | 9/1993 | Murji et al. |
| 5,387,385 | A | 2/1995 | Murji et al. |
| 5,455,992 | A * | 10/1995 | Kurschatke et al. ............. 26/99 |
| 5,518,801 | A | 5/1996 | Chappell et al. |
| 5,562,645 | A | 10/1996 | Tanzer et al. |
| 5,634,915 | A | 6/1997 | Osterdahl |
| 5,641,441 | A | 6/1997 | Yang |
| 5,691,035 | A | 11/1997 | Chappell et al. |
| 5,704,101 | A | 1/1998 | Majors et al. |
| 5,723,087 | A | 3/1998 | Chappell et al. |
| 5,743,999 | A | 4/1998 | Kamps et al. |
| 5,891,544 | A | 4/1999 | Chappell et al. |
| 5,916,507 | A | 6/1999 | Dabi et al. |
| 5,916,663 | A | 6/1999 | Chappell et al. |
| 5,925,299 | A | 7/1999 | Dierckes et al. |
| 6,007,468 | A | 12/1999 | Giacometti |
| 6,027,483 | A | 2/2000 | Chappell et al. |
| 6,053,232 | A | 4/2000 | Biagotti |
| 6,074,524 | A | 6/2000 | Wu et al. |
| 6,203,654 | B1 * | 3/2001 | McFall et al. ................ 156/268 |
| 6,264,872 | B1 | 7/2001 | Majors et al. |
| 6,296,737 | B1 | 10/2001 | Wu et al. |
| 6,344,109 | B1 | 2/2002 | Gross |
| 6,344,111 | B1 | 2/2002 | Wilhelm |
| 6,355,200 | B1 | 3/2002 | Schmidt et al. |
| 6,383,431 | B1 * | 5/2002 | Dobrin et al. ................ 264/154 |
| 6,458,447 | B1 | 10/2002 | Cabell et al. |
| 6,533,898 | B2 | 3/2003 | Gross |
| 6,608,236 | B1 | 8/2003 | Hetzler et al. |
| 6,739,024 | B1 | 5/2004 | Wagner |
| 6,913,718 | B2 * | 7/2005 | Ducker et al. ............... 264/37.1 |
| 7,112,257 | B2 | 9/2006 | Baggot et al. |
| 7,497,926 | B2 | 3/2009 | Hermans et al. |
| 7,527,615 | B2 | 5/2009 | Roe et al. |
| 7,632,979 | B2 | 12/2009 | Fujii et al. |
| 7,772,457 | B2 | 8/2010 | Ohtsuka et al. |
| 7,799,176 | B2 | 9/2010 | Schulz |
| 8,021,591 | B2 | 9/2011 | Curro et al. |
| 8,502,013 | B2 | 8/2013 | Zhao et al. |
| 2002/0119720 | A1 | 8/2002 | Aurora et al. |
| 2003/0121380 | A1 | 7/2003 | Cowell et al. |
| 2003/0204178 | A1 | 10/2003 | Febo et al. |
| 2005/0021753 | A1 | 1/2005 | Coleman |
| 2005/0064136 | A1 | 3/2005 | Turner et al. |
| 2005/0173085 | A1 | 8/2005 | Schulz |
| 2006/0087053 | A1 | 4/2006 | O'Donnell et al. |
| 2006/0151914 | A1 | 7/2006 | Gerndt et al. |
| 2006/0206072 | A1 | 9/2006 | Malakouti et al. |
| 2006/0286343 | A1 | 12/2006 | Curro et al. |
| 2008/0167634 | A1 | 7/2008 | Kouta et al. |
| 2008/0217809 | A1 | 9/2008 | Zhao et al. |
| 2008/0221538 | A1 | 9/2008 | Zhao et al. |
| 2008/0221539 | A1 | 9/2008 | Zhao et al. |
| 2008/0221541 | A1 | 9/2008 | Lavash et al. |
| 2008/0221542 | A1 | 9/2008 | Zhao et al. |
| 2009/0087636 | A1 | 4/2009 | Yasuda et al. |
| 2010/0201024 | A1 | 8/2010 | Gibson et al. |
| 2010/0318047 | A1 | 12/2010 | Ducker et al. |
| 2012/0064280 | A1 | 3/2012 | Hammons et al. |
| 2012/0064298 | A1 | 3/2012 | Orr et al. |
| 2012/0273146 | A1 | 11/2012 | Curro et al. |
| 2012/0273148 | A1 | 11/2012 | Orr et al. |
| 2012/0273997 | A1 | 11/2012 | Stone et al. |
| 2012/0276238 | A1 | 11/2012 | Strube et al. |
| 2012/0276239 | A1 | 11/2012 | Coe et al. |
| 2012/0276337 | A1 | 11/2012 | Curro et al. |
| 2012/0276341 | A1 | 11/2012 | Lake et al. |
| 2012/0277393 | A1 | 11/2012 | Curro et al. |
| 2012/0277701 | A1 | 11/2012 | Stone et al. |
| 2012/0277704 | A1 | 11/2012 | Marinelli et al. |
| 2012/0277705 | A1 | 11/2012 | Marinelli et al. |
| 2012/0277706 | A1 | 11/2012 | Marinelli et al. |
| 2012/0277707 | A1 | 11/2012 | Orr et al. |
| 2012/0277708 | A1 | 11/2012 | Marinelli et al. |
| 2012/0277709 | A1 | 11/2012 | Marinelli et al. |

FOREIGN PATENT DOCUMENTS

| | | |
|---|---|---|
| JP | H05-084262 | 4/1993 |
| JP | H-10-309298 | 11/1998 |
| JP | H10-309298 | 11/1998 |
| JP | H11-318982 | 11/1999 |
| JP | A-2008-132055 | 6/2008 |
| WO | WO 01/85083 A1 | 11/2001 |
| WO | WO 03/041751 | 5/2003 |
| WO | WO 2005/011936 A1 | 2/2005 |
| WO | WO 2005011936 A1 * | 2/2005 |
| WO | WO 2008/107846 | 9/2008 |
| WO | WO 2011/009997 A2 | 1/2011 |

OTHER PUBLICATIONS

U.S. Appl. No. 13/094,559, filed Apr. 26, 2011, Richard George Coe et al.
U.S. Appl. No. 13/094,593, filed Apr. 26, 2011, Keith Joseph Stone et al.
U.S. Appl. No. 13/094,185, filed Apr. 26, 2011, John Lee Hammons et al.
U.S. Appl. No. 13/094,195, filed Apr. 26, 2011, Kirk Wallace Lake et al.
U.S. Appl. No. 13/094,206, filed Apr. 26, 2011, Jill Marlene Orr et al.
U.S. Appl. No. 13/094,219, filed Apr. 26, 2011, John Brian Strube et al.
U.S. Appl. No. 13/094,265, filed Apr. 26, 2011, Luigi Marinelli et al.
U.S. Appl. No. 13/094,279, filed Apr. 26, 2011, Luigi Marinelli et al.
U.S. Appl. No. 13/094,295, filed Apr. 26, 2011, Luigi Marinelli et al.
U.S. Appl. No. 13/094,310, filed Apr. 26, 2011, Jill Marlene Orr et al.
U.S. Appl. No. 13/455,185, filed Apr. 25, 2012, Luigi Marinelli et al.
U.S. Appl. No. 13/455,190, filed Apr. 25, 2012, Luigi Marinelli et al.
U.S. Appl. No. 13/455,199, filed Apr. 25, 2012, Jill Marlene Orr et al.
U.S. Appl. No. 13/455,508, filed Apr. 25, 2012, John Joseph Curro et al.
U.S. Appl. No. 13/455,532, filed Apr. 25, 2012, John Joseph Curro et al.
U.S. Appl. No. 13/455,698, filed Apr. 25, 2012, John Joseph Curro et al.
International Search Report dated Sep. 14, 2012, 8 pages.
International Search Report dated Aug. 9, 2012, 12 pages.
International Search Report dated Sep. 19, 2012, 8 pages.
All Office Actions, U.S. Appl. No. 13/455,532.
All Office Actions, U.S. Appl. No. 13/094,310.
All Office Actions, U.S. Appl. No. 13/455,199.

(56) References Cited

OTHER PUBLICATIONS

All Office Actions, U.S. Appl. No. 13/094,295.
All Office Actions, U.S. Appl. No. 13/455,532, Case No. 12439.
All Office Actions, U.S. Appl. No. 13/455,190.
All Office Actions, U.S. Appl. No. 13/094,279.
All Office Actions, U.S. Appl. No. 13/455,185.
All Office Actions, U.S. Appl. No. 13/094,265.
All Office Actions, U.S. Appl. No. 13/455,508.
Office Action dated Feb. 25, 2016, U.S. Appl. No. 13/094,295.

* cited by examiner

METHODS OF MAKING ABSORBENT MEMBERS HAVING DENSITY PROFILE

CROSS-REFERENCE TO RELATED APPLICATIONS

This application is a continuation-in-part of U.S. patent application Ser. No. 13/094,295 filed on Apr. 26, 2011.

FIELD OF THE INVENTION

The present invention is directed to absorbent members and methods of making the same, and more particularly to absorbent members and methods of making the same that provide the absorbent members with a controlled density profile.

BACKGROUND OF THE INVENTION

Currently, some disposable absorbent articles such as diapers, sanitary napkins, and pantiliners are provided with a low density airfelt absorbent core. Airfelt, or comminuted wood pulp, is typically made in a process that involves several steps. The first step is one in which pulp fibers are suspended in water and introduced to a moving screen from the headbox in a wetlaid paper process. The water is removed by a combination of gravity and vacuum before introduction to a drying process to form a relatively high basis weight material that is referred to as "drylap". Drylap may be in sheet or roll form. Thereafter, the drylap is shipped to the absorbent article manufacturer. The absorbent article manufacturer subjects the drylap to comminution process or shredding to make airfelt or "fluff" via an airlaid process. This is typically done on-line in an absorbent article manufacturing line.

Airfelt has several limitations when used as an absorbent core material in disposable absorbent articles. Airfelt typically has low integrity, and is subject to bunching and roping when wet. Airfelt typically has a low density and cannot provide as much capillary work potential as a higher density material. In addition, airfelt has the same density throughout the thickness, and is not readily formed into structures having a density gradient should it be desired to provide a core structure with zones having different properties.

Airlaid structures are another type of absorbent material commonly used in absorbent articles. The air laying process involves the comminution or shredding of drylap to make airfelt or "fluff". Binder materials, such as latex binder, may then be added to provide strength and integrity to the material. Super-absorbent polymers are often added in the air laying process as well. Airlaid structures can be formed in a manner which does provide a density gradient, as in US 2003/0204178 A1, but this involves more expensive processes and materials. The air laying process is often done at an intermediate supplier, resulting in added cost for shipping the material to the converting operation. The combination of more costly materials, processing and shipping result in a significantly more expensive material and a more complex supply chain.

Various different absorbent structures and other structures used in absorbent articles, and methods of making the same, are disclosed in the patent literature, including: U.S. Pat. No. 3,017,304, Burgeni; U.S. Pat. No. 4,189,344, Busker; U.S. Pat. No. 4,992,324, Dube; U.S. Pat. No. 5,143,679, Weber; U.S. Pat. No. 5,242,435, Murji; U.S. Pat. No. 5,518,801, Chappell, et al.; U.S. Pat. No. 5,562,645, Tanzer, et al.; U.S. Pat. No. 5,743,999, Kamps; U.S. Patent Application Publication No. 2003/0204178 A1, Febo, et al.; U.S. Patent Application Publication No. 2006/0151914, Gerndt; U.S. Patent Application Publication No. 2008/0217809 A1, Zhao, et al.; U.S. Patent Application Publication No. 2008/0221538 A1, Zhao, et al.; U.S. Patent Application Publication No. 2008/0221539 A1, Zhao, et al.; U.S. Patent Application Publication No. 2008/0221541 A1, Lavash, et al.; U.S. Patent Application Publication No. 2008/0221542 A1, Zhao, et al.; and, U.S. Patent Application Publication No. 2010/0318047 A1, Ducker, et al. However, the search for improved absorbent structures and methods of making the same has continued.

It is desirable to provide improved absorbent members and methods of making the same. In particular, it is desirable to provide absorbent members with improved liquid acquisition, flexibility, tensile strength, and fluid retention. Ideally, it is desirable to produce such improved absorbent members at a low cost.

SUMMARY OF THE INVENTION

The present invention is directed to absorbent members and methods of making the same. There are numerous non-limiting embodiments of these members and methods, and more particularly to absorbent members and methods of making the same that may be used to provide the absorbent members with a controlled density profile.

In one non-limiting embodiment, the absorbent structure comprises at least one unitary absorbent fibrous layer or web comprising at least some cellulose fibers. The fibrous layer has a first surface, a second surface, a length, a width, a thickness, and a density profile through its thickness. The density profile may be substantially continuous through the thickness of the fibrous layer. The fibrous layer may further comprise different regions throughout the x-y plane with density profiles through their thicknesses. The thickness of the fibrous layer can be divided into a range of distances measured through its thickness from 0% at its first surface to 100% of the distance through its thickness at its second surface. In certain embodiments, the absorbent layer comprises a location that has a maximum density and a portion or portions with a minimum density. The mean maximum density measurement through the thickness of the layer may be at least about 1.2 times the mean density of the portion or portions with the minimum density. In one non-limiting embodiment, the fibrous layer has a density profile that is relatively centered in which: (a) the maximum density of the layer is located between about 35% and about 65%, alternatively between about 40% and about 60%, of the distance through the thickness of the layer; and (b) the mean maximum density measurement through the thickness of the layer is at least 1.2 times the mean density of the layer measured at outer zones of the layer where the outer zones of the layer are: (1) between 5% to 15%; or (2) between 85% and 95% of the thickness of the layer.

In other embodiments, the density profile of the fibrous layer is skewed toward one of the surfaces of the fibrous layer. In such embodiments, (a) the maximum density of the layer is located outside of the zone of the layer that is between about 35% and about 65%, alternatively between about 40% and about 60%, of the distance through the thickness of the layer; and (b) the mean maximum density measurement through the thickness of the layer is at least 1.2 times the mean density of the web measured at outer zones of the layer that are: (i) between 5% to 15%; or (ii) between 85% and 95% of the thickness of the layer.

Other embodiments are possible. For example, the absorbent members described above can be further compacted in regions, or over their entire surface. In other embodiments, the web can have different regions with different density profiles. In other embodiments, the absorbent members can be provided with a three-dimensional topography. In still other embodiments, the absorbent members can be apertured.

The methods of forming the absorbent members involve subjecting a precursor web to at least one cycle (or pass) through a mechanical deformation process. The precursor material may be in roll or sheet form (e.g., sheet pulp). The precursor material may comprise any suitable wet laid cellulose-containing material, including but not limited to: drylap, liner board, paper board, post-consumer recycled material, filter paper, and combinations thereof. The methods may involve passing the precursor web through a pair of counter-rotating rolls. The surface of the individual rolls may, depending on the desired type of deformation, be: smooth (i.e., an anvil roll) or provided with forming elements comprising protrusions or "male" elements. Typically, the methods involve subjecting the precursor web to multiple cycles (or passes) through a mechanical deformation process. The mechanical deformation process may utilize a "nested" roll arrangement in which there are at least four rolls and at least two of the rolls define two or more nips with the other rolls.

The methods described herein may be used for a variety of purposes. Such purposes can range from serving as a pre-processing step prior to feeding the precursor material into a hammer mill in order to reduce the energy required to defibrillate the material in the hammer mill, to serving as a unit operation in an absorbent article manufacturing line in order to prepare a completed absorbent member that is ready for use in an absorbent article being made on the line.

BRIEF DESCRIPTION OF THE DRAWINGS

The following detailed description will be more fully understood in view of the drawings in which.

Figure 1:
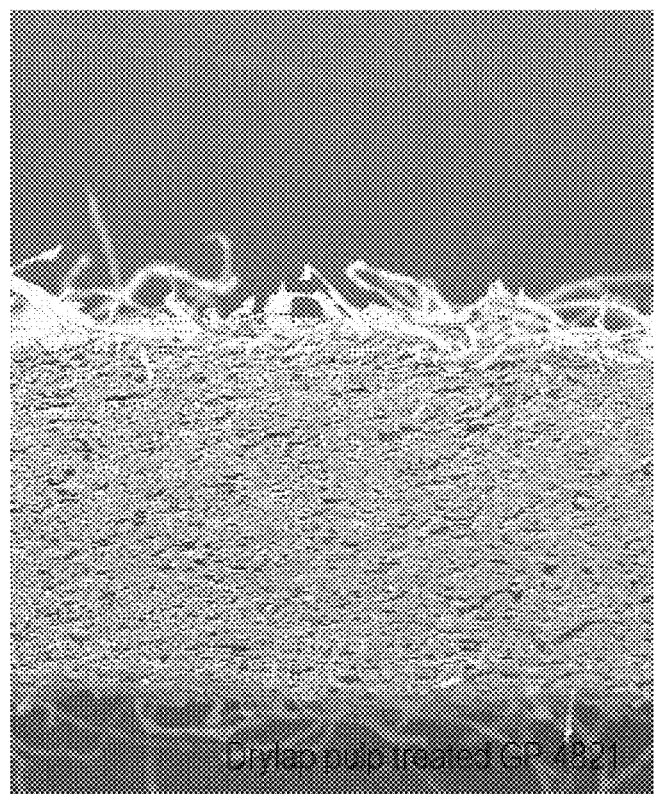
FIG. 1 is a scanning electron microscope (SEM) image of the cross-section of a web of dry lap.

The embodiments of the absorbent structure and methods of making the same shown in the drawings are illustrative in nature and are not intended to be limiting of the invention defined by the claims. Moreover, the features of the invention will be more fully apparent and understood in view of the detailed description.

DETAILED DESCRIPTION

Definitions:

The term "absorbent article" includes disposable articles such as sanitary napkins, panty liners, tampons, interlabial devices, wound dressings, diapers, adult incontinence articles, wipes, and the like. Still further, the absorbent members produced by the methods and apparatuses disclosed herein can find utility in other webs such as scouring pads, dry-mop pads (such as SWIFFER® pads), and the like. At least some of such absorbent articles are intended for the absorption of body liquids, such as menses or blood, vaginal discharges, urine, and feces. Wipes may be used to absorb body liquids, or may be used for other purposes, such as for cleaning surfaces. Various absorbent articles described above will typically comprise a liquid pervious topsheet, a liquid impervious backsheet joined to the topsheet, and an absorbent core between the topsheet and backsheet.

The term "absorbent core", as used herein, refers to the component of the absorbent article that is primarily responsible for storing liquids. As such, the absorbent core typically does not include the topsheet or backsheet of the absorbent article.

The term "absorbent member", as used herein, refers to the components of the absorbent article that typically provide one or more liquid handling functionality, e.g., liquid acquisition, liquid distribution, liquid transportation, liquid storage, etc. If the absorbent member comprises an absorbent core component, the absorbent member can comprise the entire absorbent core or only a portion of the absorbent core.

The term "absorbent structure", as used herein, refers to an arrangement of more than one absorbent component of an absorbent article.

The terms "compaction" and "re-densification", as used herein, refer to a process step in which the density of a web is increased.

The term "cross direction" means the path that is perpendicular to the machine direction in the plane of the web.

The term "de-densification", as used herein, refers to a "density reduction" in which the density of a web is reduced.

The term "density profile", as used herein, refers to a change in density through the thickness of an absorbent member, and is distinguishable from ordinary variations in the density of absorbent members having a substantially uniform density throughout the thickness. The density profile can be in any of the configurations described herein. Density profiles may be illustrated in photomicrographs, SEM and Micro CT Scan images.

The term "discrete", as used herein, means distinct or unconnected. When the term "discrete" is used relative to forming elements on a forming member, it is meant that the distal (or radially outwardmost) ends of the forming elements are distinct or unconnected in both the machine direction and cross-machine direction (even though bases of the forming elements may be formed into the same surface of a roll, for example). For example, the ridges on a ring roll are not considered to be discrete.

The term "disposable" is used herein to describe absorbent articles which are not intended to be laundered or otherwise restored or reused as an absorbent article (i.e., they are intended to be discarded after use and, preferably, to be recycled, composted or otherwise disposed of in an environmentally compatible manner).

The term "drylap", as used herein, refers to a dried, wetlaid cellulose-containing fibrous material that may be in roll or sheet form. Drylap is also known as fluff pulp or communition pulp. For some applications, drylap comprises SBSK (Southern Bleached Softwood Kraft) or NBSK (Northern Bleached Softwood Kraft) pulp produced in relatively heavy caliper, high basis weight sheet form. The sheet product is rewound into continuous rolls or stacks of sheets for shipment to a disposable article manufacturer. At the manufacturer's plant, the rolls are continuously fed into a device, such as a hammermill, to be reduced as much as reasonably possible to individual fibers thereby creating cellulose "fluff". Alternatively, drylap grades of material can be de-densified by the processes described herein. In addition to cellulose fibers, drylap can include fibers of rayon, polyester, cotton, post-consumer recycled material, other fibrous materials, or even particulate additives comprising items such as mineral fillers, Kaolin clay, or powdered cellulose. Drylap materials of the type useful in this invention include those described in U.S. Pat. Nos. 6,074,524 and 6,296,737.

The terms "exterior", "outer", and "outside", as used herein with reference to zones of an absorbent member, refer to those zones that are spaced in the z-direction away from a plane that runs through the center of the absorbent member.

The term "joined to" encompasses configurations in which an element is directly secured to another element by affixing the element directly to the other element; configurations in which the element is indirectly secured to the other element by affixing the element to intermediate member(s) which in turn are affixed to the other element; and configurations in which one element is integral with another element, i.e., one element is essentially part of the other element. The term "joined to" encompasses configurations in which an element is secured to another element at selected locations, as well as configurations in which an element is completely secured to another element across the entire surface of one of the elements.

The term "layer" is used herein to refer to an absorbent member whose primary dimension is X-Y, i.e., along its length and width. It should be understood that the term "layer" is not necessarily limited to single layers or sheets of material. Thus the layer can comprise laminates or combinations of several sheets or webs of the requisite type of materials. Accordingly, the term "layer" includes the terms "layers" and "layered".

The term "machine direction" means the path that material, such as a web, follows through a manufacturing process.

The terms "mechanically impacting" or "mechanically deforming", may be used interchangeably herein, to refer to processes in which a mechanical force is exerted upon a material.

The term "Micro-SELF" is a process that is similar in apparatus and method to that of the SELF process defined herein. Micro-SELF teeth have different dimensions such that they are more conducive to forming tufts with openings on the leading and trailing ends. A process using micro-SELF to form tufts in a web substrate is disclosed in U.S. Patent application Publication No. US 2006/0286343A1.

The term "paper board", as used herein, refers to the class of heavyweight paper and other fiberboards thicker than 0.15 millimeter, including boxboard, cardboard, chipboard, containerboard, corrugated board, and linerboard.

The term "patterned", as used herein with reference to the forming members, includes forming members having discrete elements thereon, as well as those having continuous features thereon such as the ridges and grooves on a ring roll.

The term "post-consumer recycled material" as used herein generally refers to material that can originate from post-consumer sources such as domestic, distribution, retail, industrial, and demolition. "Post-consumer fibers" means fibers obtained from consumer products that have been discarded for disposal or recovery after having completed their intended uses and is intended to be a subset of post consumer recycled materials. Post-consumer materials may be obtained from the sorting of materials from a consumer or manufacturer waste stream prior to disposal. This definition is intended to include materials which are used to transport product to a consumer, including, for example, corrugated cardboard containers.

The term "region(s)" refer to portions or sections across the X-Y plane of the absorbent member.

The terms "ring roll" or "ring rolling" refer to a process using deformation members comprising counter rotating rolls, intermeshing belts or intermeshing plates containing continuous ridges and grooves where intermeshing ridges and grooves of deformation members engage and stretch a web interposed therebetween. For ring rolling, the deformation members can be arranged to stretch the web in the cross machine direction or the machine direction depending on the orientation of the teeth and grooves.

The term "rotary knife aperturing" (RKA) refers to a process and apparatus using intermeshing deformation members similar to that defined herein with respect to SELF or micro-SELF. The RKA process differs from SELF or micro-SELF in that the relatively flat, elongated teeth of a SELF or micro-SELF deformation member have been modified to be generally pointed at the distal end. Teeth can be sharpened to cut through as well as deform a web to produce an apertured web, or in some cases, a three-dimensionally apertured web, as disclosed in U.S. Patent Application Publication Nos. US 2005/0064136A1, US 2006/0087053A1, and US 2005/021753. RKA teeth can have other shapes and profiles and the RKA process can also be used to mechanically deform fibrous webs without aperturing the web. In other respects such as tooth height, tooth spacing, pitch, depth of engagement, and other processing parameters, RKA and the RKA apparatus can be the same as described herein with respect to SELF or micro-SELF.

The terms "SELF" or "SELF'ing", refer to Procter & Gamble technology in which SELF stands for Structural Elastic Like Film. While the process was originally developed for deforming polymer film to have beneficial structural characteristics, it has been found that the SELF'ing process can be used to produce beneficial structures in other materials, such as fibrous materials. Processes, apparatus, and patterns produced via SELF are illustrated and described in U.S. Pat. Nos. 5,518,801; 5,691,035; 5,723,087; 5,891,544; 5,916,663; 6,027,483; and, 7,527,615 B2.

The term "unitary structure", as used herein, refers to a structure that either comprises: a single layer, or comprises fully-integrated multiple layers that are held together by hydrogen bonding and mechanical entanglement, and are not formed by assembling multiple layers that are formed separately and joined together with attachment means such as glue. An example of a unitary structure is a structure comprising different types of fibers (such as eucalyptus fibers that may be laid down over other cellulose fibers to form the outer layers for softness in tissue making).

The term "upper" refers to absorbent members, such as layers, that are nearer to the wearer of the absorbent article during use, i.e. towards the topsheet of an absorbent article; conversely, the term "lower" refers to absorbent members that are further away from the wearer of the absorbent article towards the backsheet. The term "laterally" corresponds to direction of the shorter dimension of the article, which generally during use corresponds to a left-to-right orientation of the wearer. "Longitudinally" then refers to the direction perpendicular to the lateral one, but not corresponding to the thickness direction.

The term "Z-dimension" refers to the dimension orthogonal to the length and width of the member, core or article. The Z-dimension usually corresponds to the thickness of the member, core or article. As used herein, the term "X-Y dimension" refers to the plane orthogonal to the thickness of the member, core or article. The X-Y dimension usually corresponds to the length and width, respectively, of the member, core or article.

The term "zone(s)" refer to portions or sections through the Z-direction thickness of the absorbent member.

I. Absorbent Members

The present invention is directed to absorbent members and methods of making the same, and more particularly to absorbent members and methods of making the same that provide the absorbent members with a controlled density profile. The methods described herein allow a number of properties of the density profile to be controlled or modulated. The location of the zone of maximum density through the thickness of the absorbent member may be controlled. The amount of the maximum density can be controlled. The thickness of the zones with higher and lower density can be controlled. The ratio of the mean maximum density to the mean density of the region(s) with lower density can be controlled. In addition, any of these properties can be modified across the length and/or width of the absorbent member.

The methods described herein can provide a density profile without the complications and expense of producing airlaid webs. The density profile, unlike that of airlaid structures formed of multiple layers, may be substantially continuous through the thickness of the fibrous web. More specifically, airlaid structures formed of multiple layers are believed to have a step-like density gradient. The density profile of the absorbent members described herein, on the other hand, may be substantially continuous through the thickness of the fibrous web (such that when graphed, the density profile may form a substantially continuous curve that is free of major step-changes and/or breaks). The absorbent members described herein may, thus, be non-airlaid. As a result, the absorbent members may be substantially free, or completely free of binder material, such as latex binders sometimes used in making airlaid materials. The absorbent members described herein may, if desired, also be substantially free, or completely free of absorbent gelling material, another common ingredient in airlaid materials. The methods described herein can provide a density profile without the complications and expense of adding water and/or heating the precursor material.

The absorbent members are made from a "precursor material" that is in the form of a web or sheet comprising at least some cellulosic material, which may be a paper grade material. The precursor material may comprise any suitable wetlaid material, including but not limited to: drylap, liner board, paper board, post-consumer recycled material, filter paper, and combinations thereof. In some cases, the absorbent members may consist of, or consist essentially of, one of these wetlaid materials.

The precursor material will typically comprise a plurality of individual fibers. A large proportion of cellulose fibers can provide for various advantages, such as keeping the cost of the web low. In particular aspects of the invention, the precursor material has a fiber content in which at least about 90 wt % of the fibers are cellulose, or fibers have a length of not more than about 0.4 inch (about 1 cm). Alternatively, at least about 95 wt %, and optionally, at least about 98 wt % of the fibers are cellulose, or fibers have a length of not more than about 0.4 inch (about 1 cm). In other desired arrangements, the precursor web can have a fiber content in which substantially about 100 wt % of the fibers are cellulose, or fibers have a length of not more than about 0.4 inch (about 1 cm).

The fibers comprising the precursor material include cellulosic fibers commonly known as wood pulp fibers. Applicable wood pulps include chemical pulps, such as Kraft, sulfite, and sulfate pulps, as well as mechanical pulps including, for example, groundwood, thermomechanical pulp and chemically modified thermomechanical pulp. Chemical pulps, however, may be preferred in certain embodiments since they may impart superior properties to the precursor material made therefrom. Pulps derived from both deciduous trees (hereinafter, also referred to as "hardwood") and coniferous trees (hereinafter, also referred to as "softwood") may be utilized. The hardwood and softwood fibers can be blended, or alternatively, can be deposited in layers to provide a stratified web. U.S. Pat. Nos. 3,994,771 and 4,300,981, describe layering of hardwood and softwood fibers. Also applicable to the present invention are fibers derived from recycled paper, which may contain any or all of the above categories as well as other non-fibrous materials such as fillers and adhesives used to facilitate the precursor web making. In addition to the above, fibers and/or filaments made from polymers, specifically hydroxyl polymers may be used in the present invention. Nonlimiting examples of suitable hydroxyl polymers include polyvinyl alcohol, starch, starch derivatives, chitosan, chitosan derivatives, cellulose derivatives, gums, arabinans, galactans and mixtures thereof.

The fibers comprising the precursor material will normally include fibers derived from wood pulp. Other natural fibers, such as cotton linters, bagasse, wool fibers, silk fibers, etc., can be utilized and are intended to be within the scope of this invention. Synthetic fibers, such as rayon, polyethylene and polypropylene fibers, may also be utilized in combination with natural cellulosic fibers. One exemplary polyethylene fiber which may be utilized is PULPEX®, available from Hercules, Inc. (Wilmington, Del.).

The fibers are typically held together by interfiber entanglement and hydrogen bonding. The fibers may have any suitable orientation. In certain precursor materials, the fibers will be aligned predominately in the direction of the process in which they were formed (or the "machine direction") of the forming process.

Figure 1A:
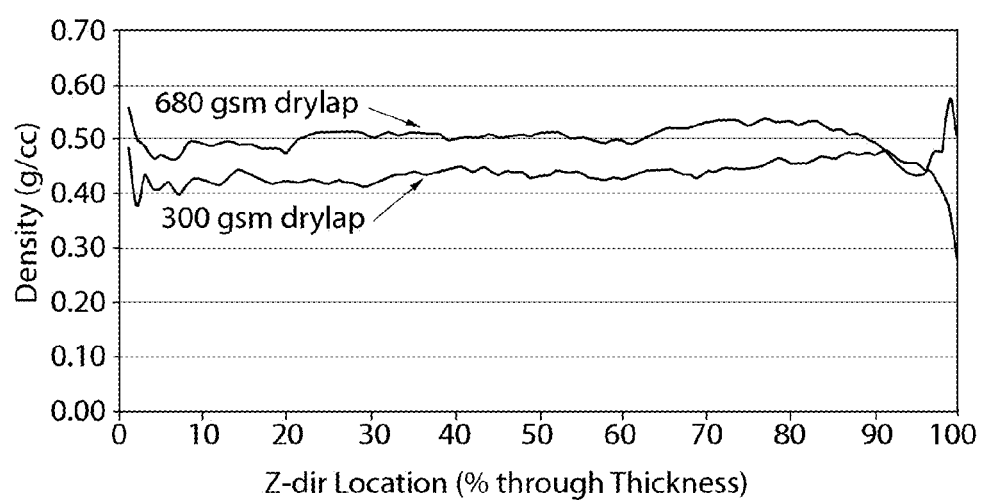
FIG. 1A is a graph of the micro CT density profile throughout the thickness of a web of dry lap.

FIG. 1 is an SEM image of one embodiment of a precursor material comprising dry lap. As shown in FIG. 1, the precursor material is a single layer structure that is generally relatively dense throughout its thickness. This precursor material is not suitable for use as a component of an absorbent article due to its lack of void volume and high stiffness. Table 1 in the Examples section shows the properties of two such precursor materials. A graph showing the density of such precursor materials with the distance through the thickness T of the precursor materials shown on the x-axis and the corresponding density of the precursor material at those locations on the y-axis are shown in FIG. 1A. Such graphs can be prepared from micro CT scans conducted in accordance with the Micro CT Scan procedure set out in the Test Methods section. As shown in FIGS. 1 and 1A, there are some less dense portions at the surface of the precursor material, but these do not comprise a significant portion of the overall thickness of the precursor material. The methods described herein reduce the overall (that is, average) density and stiffness of the drylap (or other precursor material) and increase its void volume in at least some zones thereof so that it is suitable for use as an absorbent member in an absorbent article. The methods may also increase the average caliper of the precursor material.

The precursor material may have any suitable properties. The burst strength of the precursor material may be as high as 1,500 kPa or more, measured according to TAPPI test method T 403 om-91 for Burst Strength. Generally, precursor materials with lower burst strengths are more easily mechanically modified to reduce their density (that is, "de-densified" by a "density reduction" process). This is shown in Table 2 in the Examples section provided at the end of this description. Table 2 shows the caliper increases are greater in drylap samples having lower burst strengths. Therefore, it may be desirable for the precursor material to have a burst strength less than 1,500, 1,400, 1,300, 1,200, 1,100, 1,000, 900, 800, 750, 700, 600, 500, 400, 300, 200, or 100 kPa, or less. The burst strength may also fall within any range between any of these burst strength numbers.

The precursor material may have any suitable caliper, basis weight, and density. Drylap generally has a caliper of at least about 0.04 inch or greater, e.g., from about 0.04 to about 0.06 inch (about 1-1.5 mm). However, applicants have had drylap specially made having calipers as low as 0.02 inch (about 0.5 mm). Thus, in some embodiments, the caliper of the precursor material may range from about 0.02 to about 0.06 inch (about 0.5-1.5 mm). Drylap that is commercially available typically has a basis weight of between about 100 and about 200 pounds/1,000 ft² (490-980 gsm). However, applicants have had drylap specially made having a basis weight as low as 20 pounds/1,000 ft² (98 gsm), or less. Thus, in some embodiments, the basis weight of the precursor material may range from about 20 pounds/ 1,000 ft² (98 gsm) to about 200 pounds/1,000 ft² (980 gsm). In some embodiments, the precursor web material may have a density of between about 0.25 g/cc and about 0.6 g/cc, or above, alternatively between about 0.3 g/cc and about 0.6 g/cc. Typically, such precursor materials will have a relatively uniform density throughout their thickness. For example, the mean maximum density measurement through the thickness of the precursor material will typically be less than or equal to about 1.1 times the mean density of the portion or portions with the minimum density.

The precursor material may have any suitable moisture content. Drylap usually has a moisture content of less than about 10 percent, e.g., about 7 percent, although lower and higher moisture contents can be used. Generally, precursor materials with lower moisture contents are more easily mechanically modified to reduce their density ("de-densified"). For example, it may be desirable for the precursor web material to have a moisture content less than or equal to 10%, 9%, 8%, 7%, 6%, 5%, 4%, 3%, 2%, 1%, or any range between any of these percentages.

The precursor material may, in certain embodiments, be treated, partially treated (that is, having treated portions and untreated portions), or untreated. If the precursor material is treated, it may be provided with any suitable treatment, including but not limited to debonders such as chemical debonders. Examples of suitable treatments are described in U.S. Pat. Nos. 6,074,524, 6,296,737, 6,344,109 B1, and 6,533,898 B2. Typically, untreated precursor materials will have a higher burst strength than treated or partially treated precursor materials. Providing the precursor material with at least some treatment in the form of a debonder can permit the precursor material to be more easily mechanically modified to decrease its density.

The absorbent members formed by the methods described herein may have any suitable overall properties. The absorbent member may have an average flexure-resistance of less than or equal to about 25N, or any lesser flexure resistance value including, but not limited to, less than or equal to about 10N. The absorbent member may have an average density range of between about 0.05-0.5 g/cc. It should be understood that the average density ranges of the various possible precursor materials and the absorbent members described herein may overlap. This is due to the wide variety of possible precursor materials. For a given precursor material, the average density of the absorbent member formed herein will be less than that of the precursor material. The methods described herein can form absorbent members with any suitable average density, including but not limited to an average density less than, equal to, or greater than 0.25 g/cc with high flexibility. The methods can also form absorbent members with any suitable thickness, including but not limited to less than or equal to 4 mm, or greater than 4 mm.

The location of the portion of the absorbent member with the maximum (or peak) density may be in the approximate center of the absorbent member (that is, approximately 50% of the distance through the thickness of the absorbent member). Alternatively, the location of the maximum density may vary by up to 30%, or more of the distance through the thickness of the absorbent member, such that it may occur anywhere between about 20% up to about 95% of the distance through the thickness of the absorbent member. The lower end of this range (for example, the 20% point) may be formed on either side of the absorbent member when it is made; however, the lower density portion of the absorbent member will typically comprise the upper surface when the absorbent member is incorporated into an absorbent article. The absorbent member may have a mean maximum density range measured at the peak and at locations +/−5% of the thickness of the absorbent member around the peak of between about 0.1-0.65 g/cc. The mean maximum density may, thus, be less than or equal to about 0.25 gm/cc, or greater than about 0.25 gm/cc. The absorbent member may have a mean minimum density range measured at the location having the minimum density and at locations +/−5% of the thickness of the absorbent member around the location having the minimum density of between about 0.02 and one of the following about: 0.15, 0.2, 0.25, 0.3, 0.35, 0.4, 0.45, 0.5, and 0.55 g/cc.

The absorbent member may have any suitable ratio of mean maximum density to mean minimum density (in the lowest density zone outside of the maximum zone, exclusive of the outermost zones that are between 0-4% and 96-100% of the distance through the thickness of the absorbent member). These outermost zones are not considered in order to reduce variability of the measurements described herein. The term "mean exterior density", as used herein, refers to the mean or average density measured at outer portions of the absorbent member that are: (1) between 5% and 15%; and (2) between 85% and 95% of the thickness of the layer. When the ratio of mean maximum density to mean exterior density is specified herein, it refers to the ratio of the mean maximum density to the outer portion that has the lowest mean density. The mean maximum density measurement through the thickness of the layer may be at least about 1.2 times the mean density of the portion or portions with the minimum density. This ratio may, for example, range from about 1.2 to about 6.5, or more.

The precursor material is modified, as described herein, in order to provide a unitary absorbent member with a density profile through the z-direction thickness of the absorbent member. The density profile can be used to provide the absorbent member with at least one relatively higher density zone or portion and at least one relatively lower density zone or portion in the z-direction. The term "relatively", as used in this context, means that these zones have a difference in density relative to each other. That is, the higher density zone has a higher density relative to the lower density zone. There may be two or more zones with different densities. These zones may be designated as first, second, third, etc. zones.

The processes described herein can be tailored to modify the precursor material into an absorbent member having many possible structures. These structures include, but are not limited to: (A) an absorbent member with a central higher density zone and outer lower density portions (referred to herein as a "two-side de-densified" absorbent member); (B) an absorbent member with a higher density portion that is skewed toward one surface of the absorbent member and a lower density portion adjacent another side of the absorbent member (referred to herein as a "one-side de-densified" absorbent member); (C) a re-densified or compacted version of absorbent members (A) or (B); (D) an absorbent member having a density profile and a three dimensional topography (3D); (E) an apertured version of absorbent members (A) though (D) described above; (F) absorbent members having X-Y regions with different densities and density profiles; and (G) alternative embodiments and combinations of any of the foregoing types of absorbent members. Each of these types of absorbent members and the methods of making the same are described in greater detail below.

A. Higher Density Central Zone ("Two-Side De-Densified") Absorbent Members

Figure 2:
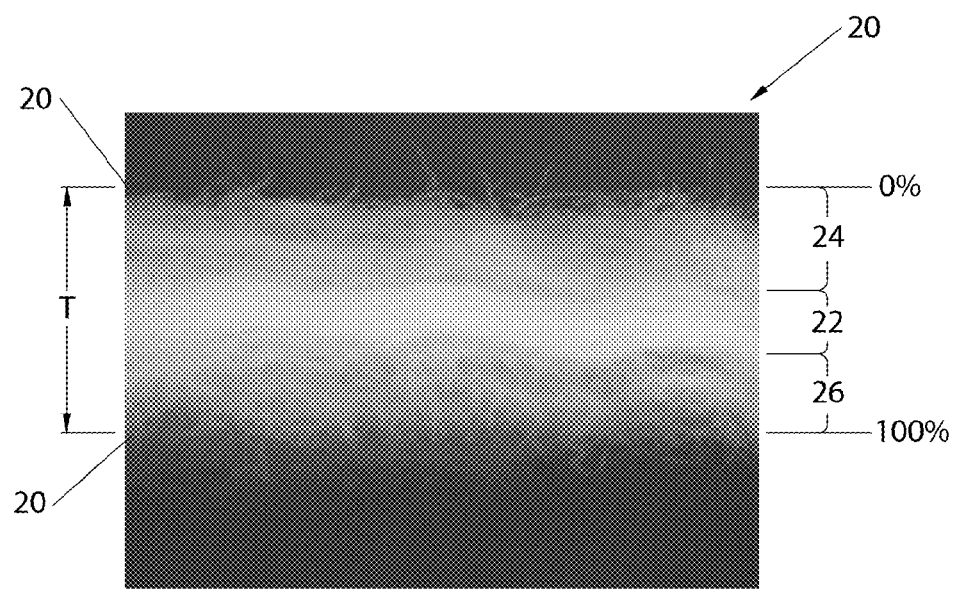
FIG. 2 is a photomicrograph of the cross-section of a web of dry lap after it has been processed according to one embodiment of the present method to form a two-side de-densified absorbent member.
Figure 3:
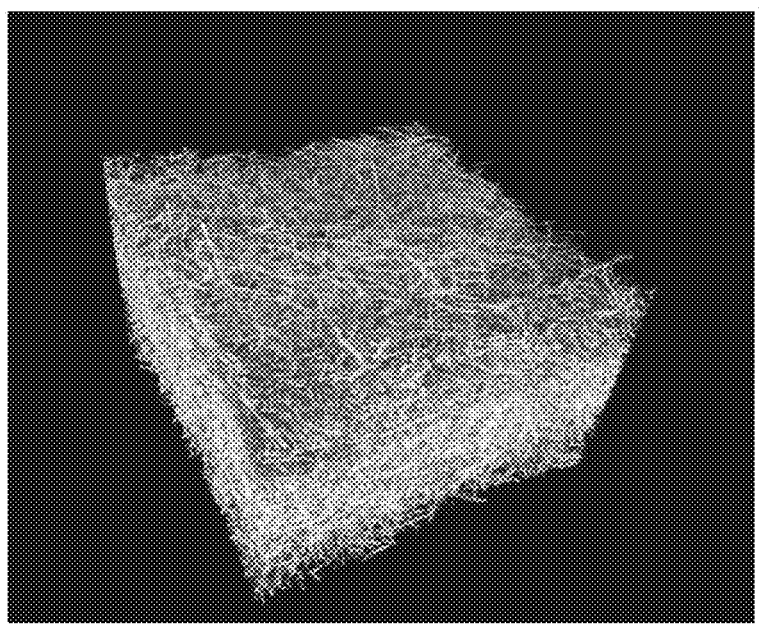
FIG. 3 is a perspective micro CT scan image of an absorbent member of the type shown in FIG. 2.

FIGS. 2 and 3 show one non-limiting embodiment of an absorbent member 20 with a higher density central zone or a ("two-side de-densified" absorbent member). The absorbent member 20 comprises a unitary absorbent fibrous layer having a first surface 20A, a second surface 20B, a length L extending in an X-direction, a width W extending in a Y-direction, and a Z-direction thickness T. As shown in FIG. 2, the thickness T of the absorbent fibrous layer can be divided into a range of distances measured through its thickness from 0% at its first surface 20A to 100% of the distance through its thickness at its second surface 20B. The absorbent fibrous layer has a density profile through its thickness T comprising a relatively higher density zone 22 disposed in the Z-direction between two relatively lower density outer zones 24 and 26 of the layer. The unitary absorbent fibrous layer may be referred to herein as the "absorbent layer", the "fibrous layer", or simply the "layer".

FIGS. 2 and 3 show that the absorbent member is expanded. By "expanded", it is meant that the fibers, particularly those in the low density portion(s), have increased void spacing therebetween in comparison to other parts of the absorbent member (such as in the higher density portion) and also in comparison to the precursor material shown in FIG. 1. Another way to describe the absorbent member is that the absorbent member is comprised of cellulose fibers that have surfaces and there are interfiber hydrogen bonds between cellulose fibers that are substantially interrupted by void spaces between the fiber surfaces. Thus, the absorbent member 20 will typically have a low density portion extending in the X-Y plane having a thickness that appears to be "fluffed up" or lofted. The lower density portion will typically be softer than the surface of the precursor web.

The surface 20A of the absorbent member 20 may, or may not, have a plurality of deformations or impact markings therein. The opposite surface 20B likewise may, or may not, have a similar pattern of deformations therein. It should be understood that in the various different embodiments of the processes described herein, the impact markings from the process may be more or less visible (or not visible) depending upon the process used and the configuration of the forming structure in the apparatus used to form the absorbent member. The deformations are present as a result of subjecting the precursor material to a mechanical deformation process which imparts localized bending, strain and shear in order to reduce the density of the precursor material. The deformations can be in any suitable form, including indentations, protrusions, or combinations thereof. The deformations can be arranged in any suitable pattern, including regular patterns or random patterns. The pattern of the deformations is a product of the process and apparatus used to reduce the density of the precursor material.

The high density portion 22 and the lower density portions 24 and 26 may comprise any suitable portion of the thickness of the absorbent member 20. The high density portion 22 may, for example, comprise between about 10%-80%, alternatively between about 10%-50%, alternatively between about 10%-25% of the thickness of the absorbent member 20. The lower density portions 24 and 26 may comprise a significant portion of the overall thickness of the absorbent member. For example, each of the lower density portions 24 and 26 (or lower density portion, if in other embodiments, there is only one low density portion) may comprise greater than, or greater than or equal to about 5%, 10%, 15%, 20%, 25%, 30%, 35%, 40%, 45%, 50%, 55%, 60%, 65%, 70%, 75%, up to about 80% of the overall thickness of the absorbent member. The thickness of the lower density portion(s) may also fall within any range between any two of the above percentages.

Figure 4:
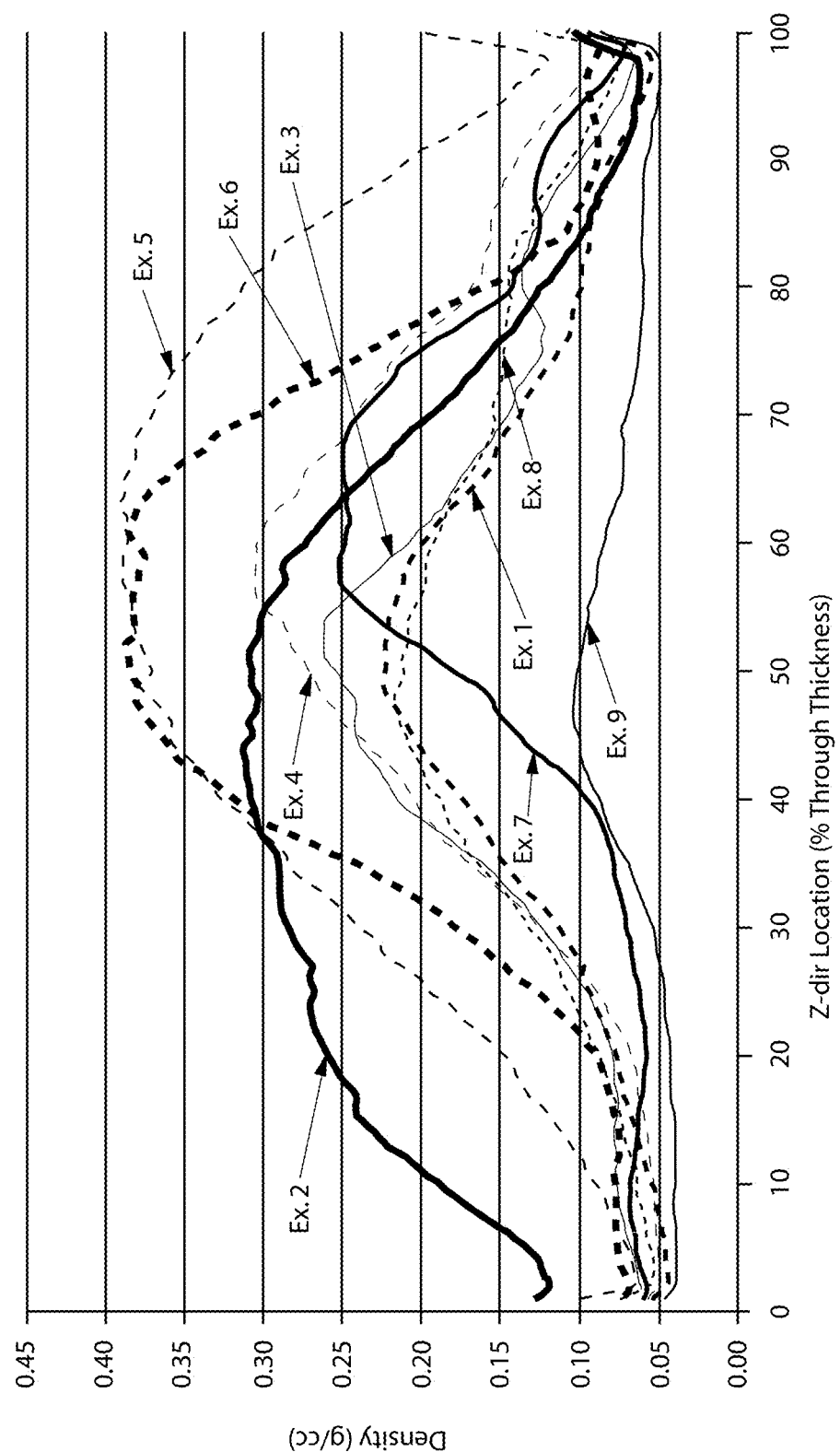
FIG. 4 is a graph of the micro CT density profile of several absorbent members such as those shown in FIGS. 2 and 3.

In a two-side de-densified structure, the absorbent member 20 may have a maximum density that is at a location between about 35% and about 65%, alternatively between about 40% and about 60% of the distance through the thickness T of the absorbent member 20. The absorbent member may have a ratio of mean maximum density to mean minimum density of greater than or equal to about 1.2, 1.3, 1.4, 1.5, 1.6, 1.7, 1.8, 1.9, 2, 2.5, 3, 3.5, 4, 4.5, 5, 5.5, 6, 6.5, or more, or any number or range of numbers between these numbers. The ratio may, for example range from about 1.2 to about 6.5, or more. Several non-limiting examples of such a structure are provided in Table 3 in the Examples below. A graph from micro CT scans showing the density profile of these members with the distance through the thickness T of the absorbent members shown on the x-axis and the corresponding density of the absorbent member at those locations on the y-axis are shown in FIG. 4.

Providing the absorbent member with a density profile may provide the absorbent member with a number of advantages. However, it should be understood that the absorbent member need not necessarily provide such advantages unless such advantages are specifically included in the appended claims.

The lower density portions 24 and 26 on at least one side of the absorbent member 20 may provide the absorbent member with void volume for faster liquid acquisition. It also provides the absorbent member 20 with a higher caliper and greater flexibility than that of the precursor material.

The higher density portion 22 may provide the absorbent member with capillary suction to lock away liquids and prevent liquids from coming out of the absorbent article. This is especially useful in reducing the tendency for body fluids to move back towards and rewet the wearer's body, (i.e., reduced rewet). The higher capillary suction may also enable the use of higher capillary suction topsheets, which may be more effective in removing bodily fluids from the wearer's body, leading to a cleaner body.

The higher density portion 22 may also provide the absorbent member with improved integrity relative to prior types of absorbent core materials, such as airfelt. Although the lower density portion will have less integrity in comparison to the higher density portion, it will also have more integrity than airfelt due to the selective breakage and preservation of hydrogen bonds. Improved integrity is characterized by improved tensile strength, which makes the absorbent material easier to process and handle during the manufacture of absorbent articles. Improved integrity may also reduce bunching, roping, and break-up of the absorbent material during wear of the absorbent article. In absorbent articles, such as sanitary napkins and pantiliners, this may lead to reduced staining visible on the body-facing side of the absorbent article.

The density profile can be provided in a unitary structure which eliminates the need to provide separate layers having different properties and bonding such layers together. This can eliminate a bonding step during processing, and eliminate the need for adhesives or other materials to hold separate layers together (which adhesives may interfere with the transportation of liquids between layers).

Absorbent members having a two-side de-densified density profile provide the greatest caliper or thickness in the fewest number of passes through a mechanical deformation process. Caliper or thickness may be of interest for those women who prefer thick sanitary napkins.

B. Skewed Density Profile or "One-Side De-Densified" Absorbent Members

Figure 5:
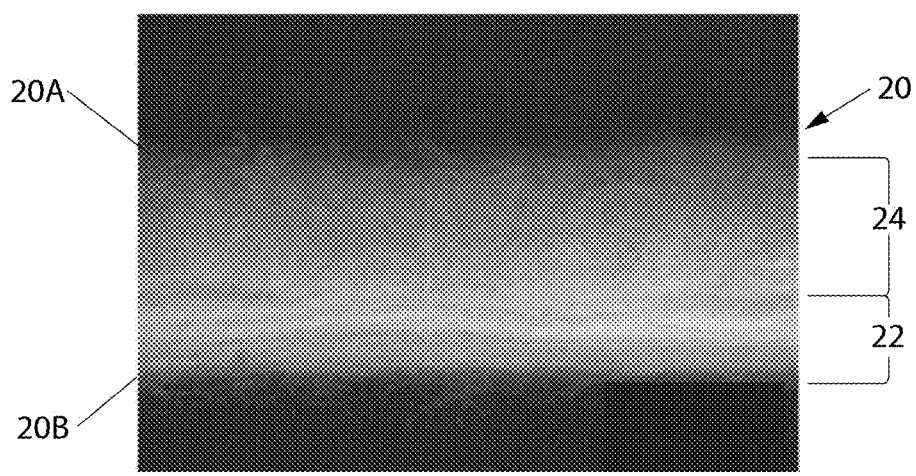
FIG. 5 is a photomicrograph of the cross-section of a web of dry lap after it has been processed according to another embodiment of the present method to form a one-side "de-densified" absorbent member.
Figure 6:
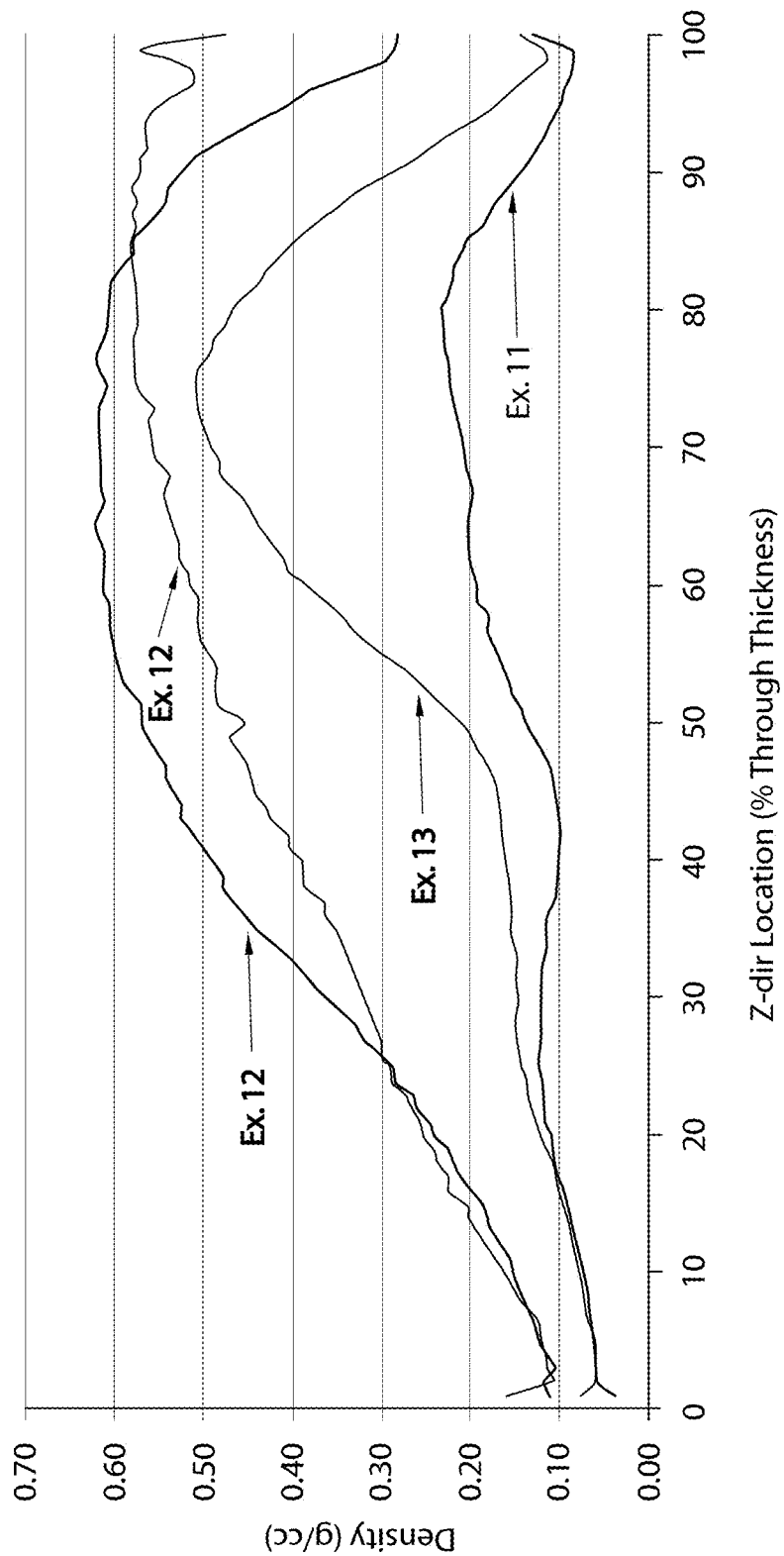
FIG. 6 is a graph of the micro CT density profile through the thickness of four absorbent members similar to the absorbent member shown in FIG. 5.

FIG. 5 shows a web of dry lap after it has been processed according to another embodiment of the methods described herein in order to form a skewed or "one-side de-densified" absorbent member 20. As shown in FIG. 5, the precursor material is formed into an absorbent member 20 that comprises a unitary absorbent fibrous layer having a higher density zone 22 adjacent one side 20B of the absorbent layer and a lower density zone 24 adjacent another side 20A of the absorbent layer. The higher and lower density zones may comprise a significant portion of the overall thickness of the absorbent member. FIG. 6 is a graph of the micro CT density profile through the thickness of four absorbent members such as that shown in FIG. 5.

In such a structure, the absorbent member 20 may have a maximum density that is at a location greater than or equal to about 60%, 65%, 70%, 75%, 80%, 90%, or 95% of the distance through the thickness T of the absorbent member, measured from either side of the absorbent member. In certain embodiments, the skewed density profiled absorbent member 20 may have a maximum density that is located outside of the zone that represents the central 20% (distances between 40-60% through the thickness), 25% (distances between 38-63% through the thickness), 30% (distances between 35-65% through the thickness), up to the central 50% (distances between 25-75% through the thickness), or 60% (distances between 20-80% through the thickness) of the thickness of the absorbent layer. The absorbent member may have a ratio of mean maximum density to mean minimum density of greater than or equal to about 1.2 to about 6.5, or more. The ratio may, for example, range from about 1.2, 1.3, 1.4, 1.5, or every additional tenth up to about 6.5, or more. Several non-limiting examples of such a structure are provided in Table 4 in the Examples section below.

When the skewed density absorbent member 20 is placed into an absorbent article comprising a liquid pervious body-facing side, a liquid impervious side, the relatively lower density outer portion 24 of the absorbent member should face the body-facing side of the absorbent article.

Absorbent members having a skewed density profile may be useful in that for a given caliper, more low density material can be located on the body-facing side of the absorbent member, which is beneficial for fluid acquisition. Positioning the high density portion on bottom pulls fluid further away from body.

C. Re-Densified/Compacted Absorbent Members

Figure 7:
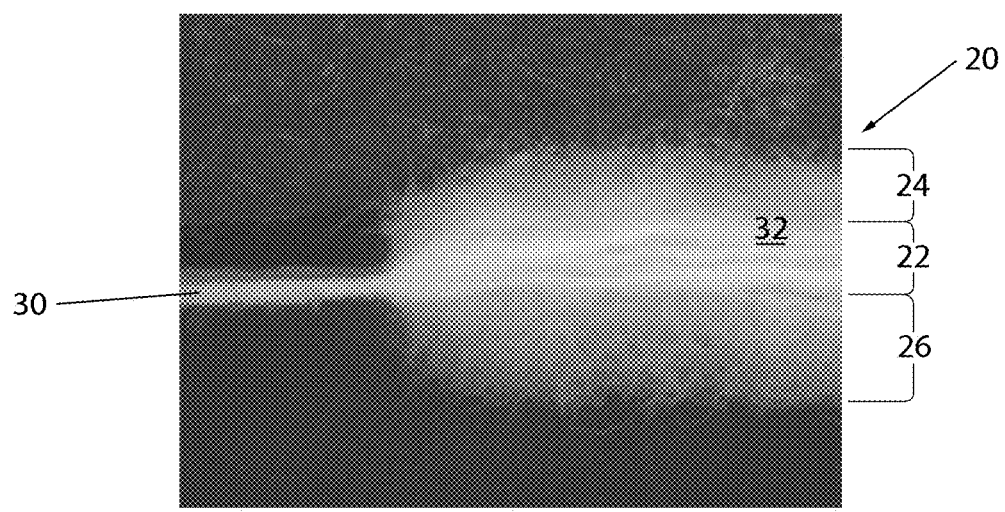
FIG. 7 is a photomicrograph of the cross-section of an absorbent member that has a portion thereof, on the left side of the image, which has been re-densified or compacted.

FIG. 7 shows a web of dry lap after it has been processed according to another embodiment of the methods described herein in order to form a re-densified or compacted absorbent member 20. In this process, the precursor material is de-densified such as described in sections IA or B above, and at least a region of the surface area of the material is then compacted. As shown in FIG. 7, the absorbent member 20 has a region 30 thereof, on the left side of the image, which has been re-densified or compacted. The region 32 of the absorbent member 20 on the right side of FIG. 7 has not been compacted and remains de-densified with a higher density central zone 22 and two lower density outer zones 24 and 26. In other embodiments, the entire absorbent member 20 may be re-densified or compacted.

The structure of a re-densified or compacted absorbent member 20 may be similar to the two-side de-densified absorbent member, or to the one-side de-densified absorbent member, depending upon which type of absorbent member was formed prior to compacting the same. In the case of the re-densified or compacted absorbent member, however, the average density of the compacted region(s) of the absorbent member will be higher (and the caliper is lower) than the absorbent member that was formed prior to compacting the same. The compacted region(s) of the absorbent member 20 may have a density of between about 0.1 g/cc and about 0.55 g/cc, while maintaining a density profile therein.

In a re-densified or compacted absorbent member, the majority of the improvement in flexibility of the de-densified absorbent member is often retained. Table 5 in the Examples section shows the difference in caliper and flexibility of a compacted two-side de-densified structure relative to an uncompacted two-side de-densified structure. Example 15 is re-densified or compacted over its entire surface area. The properties of the different regions of embodiments in which only regions of the absorbent member 20 are compacted (as opposed to the entire absorbent member 20 being compacted) are described in greater detail herein in the section I F.

Absorbent members having a re-densified or compacted density profile can be useful in that thinness may provide discretion, which is important for some consumers. A less preferred alternative approach to the re-densification/compaction process described herein would be to attempt to form a thinner absorbent member by mechanically working the precursor material less, such as by fewer passes through a mechanical deformation process. This will result in less de-densification and less caliper build. However, such an absorbent member will remain relatively stiff because many of the hydrogen bonds in the precursor material will still be present. The compaction approach allows much greater flexibility to be achieved to form thin absorbent members versus the alternative approach of subjecting the precursor material to fewer passes through a mechanical deformation process. Table 6 shows an example where a de-densified and compacted absorbent member (Example 17) is thinner and more flexible than an absorbent member (Example 16) processed with fewer passes.

D. Three Dimensional Absorbent Members

Figure 8:
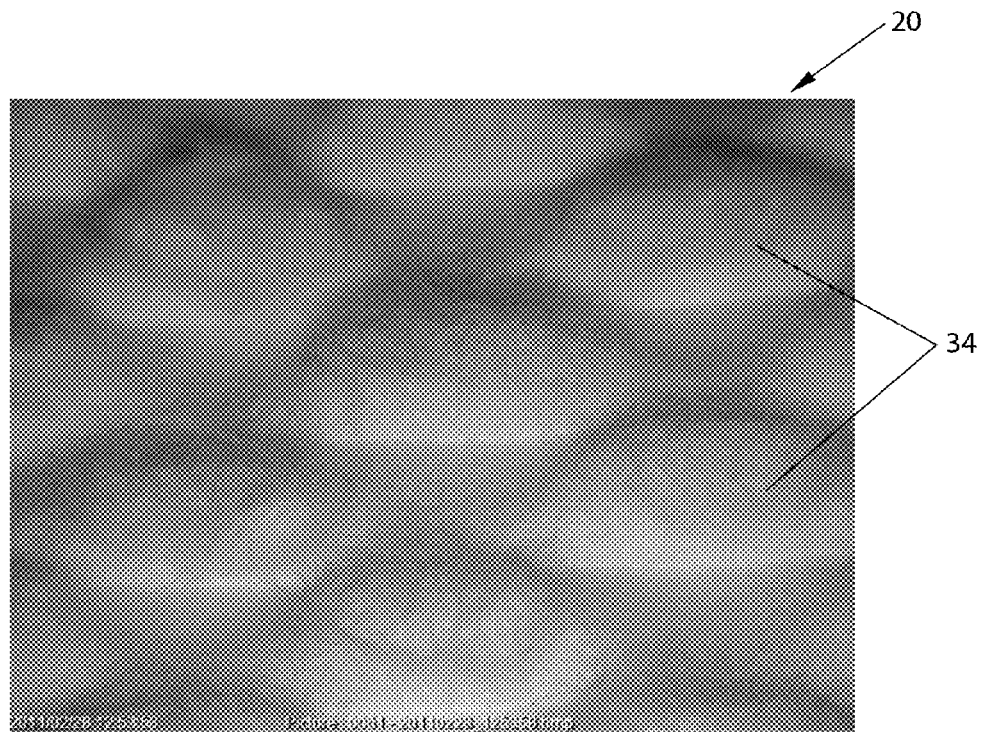
FIG. 8 is a photograph of a web of dry lap after it has been processed according to another embodiment of the methods described herein in order to form a three dimensional absorbent member.

FIG. 8 shows a web of dry lap after it has been processed according to another embodiment of the methods described herein in order to form a three dimensional absorbent member 20. In this process, the precursor material can be subjected to a process for forming a three dimensional structure into the same before and/or after it is de-densified as described in sections IA or B above.

The micro-structure of a three dimensional absorbent member 20 may be similar to the two-side de-densified absorbent member, or to the one-side de-densified absorbent member, depending upon which type of absorbent member was formed prior to or after subjecting the same to a step of forming a three dimensional topography thereon. In this embodiment, the absorbent member 20 has a density profile and further comprises a three dimensional surface topography. More specifically, at least one of the first surface and second surface comprises protrusions 34 and/or depressions. The depressions in one surface of the absorbent member 20 will typically correspond to protrusions 34 in the other surface. At least some of the protrusions 34 may have a density profile through their thickness wherein the mean maximum density is between about 1.2 and about 6.5, or more, times the mean density of those portion(s) through the thickness of the protrusions with the minimum density. If the precursor material comprises multiple layers, the protrusions may be formed in such multiple layers.

The three dimensional absorbent member 20 can have any suitable number of protrusions 34 and/or depressions therein, from one protrusion 34 or depression to a plurality of protrusions 34 and/or depressions. The protrusions 34 and/or depressions can cover any desired portion of the area of the absorbent member. In some embodiments, the protrusions 34 and/or depressions may be located in a region comprising only a portion of the area of the absorbent member. In other embodiments, the protrusions 34 and/or depressions may be distributed across substantially the entire absorbent member.

Absorbent members having a density profile and a three dimensional structure may be useful in that the protrusions provide an increase in overall caliper (which may be important for consumers who prefer thick absorbent articles).

E. Apertured Absorbent Members

Figure 9:
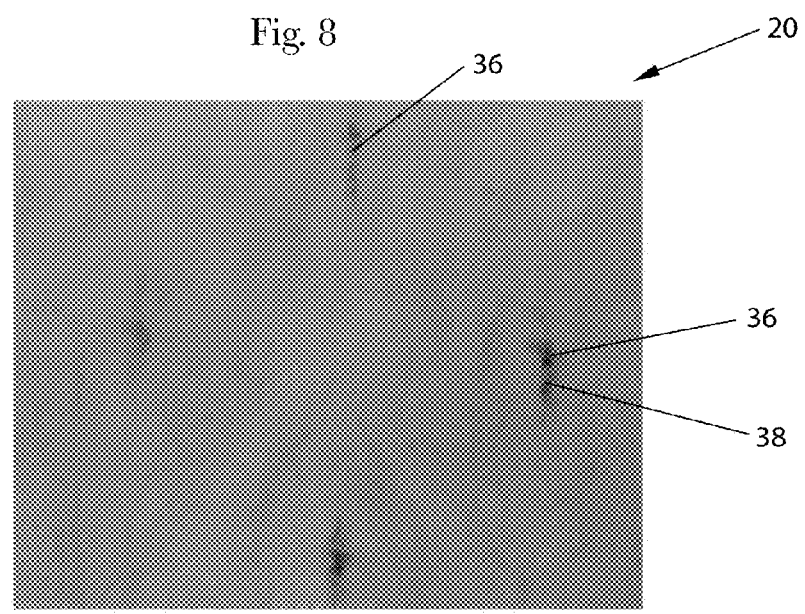
FIG. 9 is a photograph of a web of dry lap after it has been processed according to another embodiment of the methods described herein in order to form an apertured absorbent member.

FIG. 9 shows a web of dry lap after it has been processed according to another embodiment of the methods described herein in order to form an apertured absorbent member 20. In this process, the precursor material is apertured before and/or after it is de-densified as described in sections IA or B above.

The structure of the apertured absorbent member 20 may be similar to the two-side de-densified absorbent member, or to the one-side de-densified absorbent member, depending upon which type of absorbent member was formed prior to aperturing the same, or the type of absorbent member that was formed after aperturing the same. In this embodiment, there is at least one aperture 36 extending between said first and second surfaces of the absorbent member 20. If the precursor material comprises multiple layers, the apertures may extend through such multiple layers. The apertures 36 may be of any suitable shape and size. Suitable shapes include, but are not limited to circular, oval, rectangular, etc. The size of the apertures 36 can, in some embodiments, range from about 0.25 mm$^2$ to about 20 mm$^2$ in area. The apertured absorbent member may comprise an area 38 at least partially surrounding at least one aperture 36 that is compacted.

The apertured absorbent member can have any suitable number of apertures 36 therein, from one aperture to a plurality of apertures. The apertures 36 can cover any desired portion of the area of the absorbent member. In some embodiments, the apertures 36 may be located in a region comprising only a portion of the area of the absorbent member. In other embodiments, the apertures 36 may be distributed across substantially the entire absorbent member.

F. Absorbent Members Having X-Y Regions with Different Densities

There are numerous possible embodiments of absorbent members having X-Y regions with different densities and/or different density profiles. In some embodiments, the entire absorbent member may have a density profile, and the absorbent member may have different regions in the X-Y plane with different densities and/or different density profiles. In other embodiments, at least a portion of the absorbent member may be de-densified, and a portion is not de-densified. In these latter embodiments, the portion of the absorbent member that is not de-densified may have a density similar to that of the precursor material. These latter embodiments will be referred to herein as absorbent members with "regional de-densification".

1. Entire Absorbent Member has Density Profile.

Figure 10:
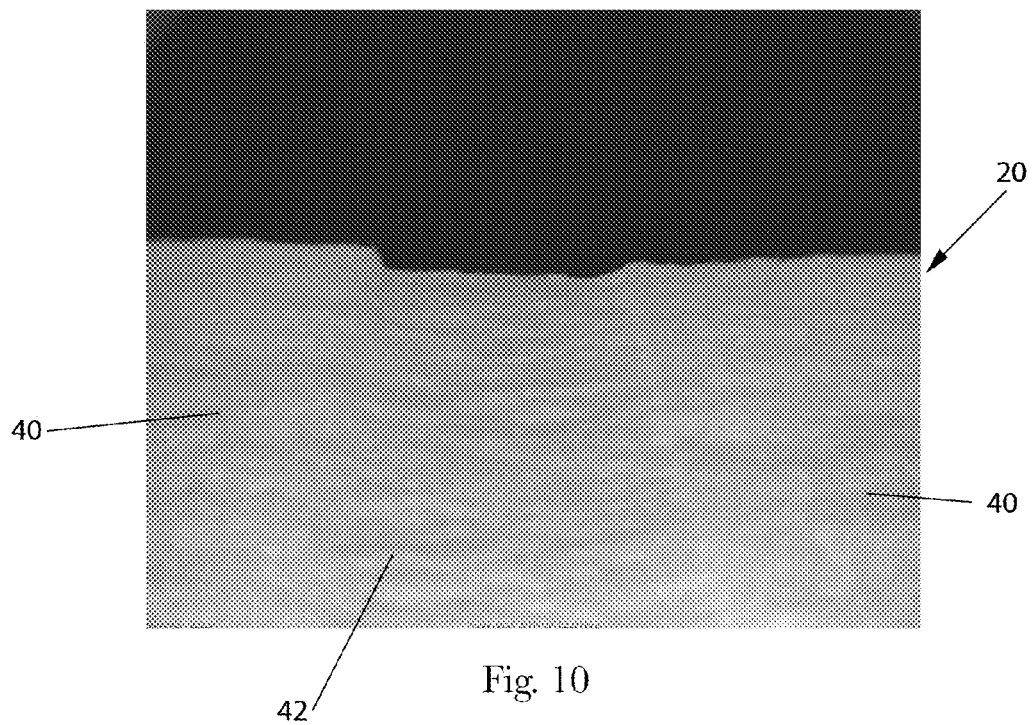
FIG. 10 is a perspective view photomicrograph of an absorbent member that has a portion thereof, in the center of the image, which has been re-densified or compacted in order to form an absorbent member having X-Y regions with different densities.

FIG. 10 shows a web of dry lap after it has been processed according to another embodiment of the methods described herein in order to form an absorbent member 20 having X-Y regions 40 and 42 with different densities and/or density profiles. In one embodiment of such a process, the precursor material is de-densified as described in sections IA or B above, and is then compacted in at least one region 42.

The structure of the regions of the absorbent member 20 with a density profile may be similar to the two-side de-densified absorbent member, or to the one-side de-densified absorbent member, depending upon which process or combination of processes was used to mechanically deform each region. The regions can have the same or different types of density profiles. For example, in the case where the types of density profiles are different, a first region can have a one-side de-densified profile, while a second region can have a two-side de-densified profile. In such embodiments, the length and width of the absorbent member define an area, and the absorbent member comprises at least two regions extending in the X and Y directions, which comprise: a) a first region comprising a portion of the area of the absorbent member, and b) a second region comprising another portion of the area of the absorbent member. The first region 40 can be said to have a first average density, a first minimum density and a first maximum density. The second region 42 has a second average density, a second minimum density and a second maximum density. In such embodiments, the second average density of the second region 42 is at least about 0.05 g/cc greater than the first average density of the first region.

The first and second regions can be of any suitable size and shape, provided that they are large enough to take a sample/specimen from the same for the purpose of the Micro CT test method described herein. Therefore, the first and second regions should each cover a region that is greater than or equal to a square having dimensions of 7.2 mm×7.2 mm (an area greater than or equal to about 52 mm$^2$). The shape of the first and second regions may be selected from the group including square, rectangular, circular, strips (which may be linear, curvilinear, or combinations thereof), irregular, combinations, and multiple regions. The size and/or shape of the first region 40 can be the same, or different from that of the second region 42.

The first and second regions 40 and 42 can cover any suitable portion of the area of the absorbent member 20 from 1%-99%, provided that the total of the areas of the two regions does not exceed 100% of the area of the absorbent member.

Numerous variations of such an embodiment are possible. For example, in some embodiments, the mean maximum densities of the first and second regions 40 and 42 may be substantially the same. As used herein, with reference to the differences in densities, the phrase "substantially the same" means that there is less than 0.05 g/cc difference between the densities. In other embodiments, the second region 42 may have a greater mean maximum density than the first region 40. In some embodiments, the second region 42 may have a lower ratio of mean maximum density to mean minimum density than the first the region. In some embodiments, the first and second regions 40 and 42 have substantially the same flexibility. As used herein, with reference to the differences in flexibility, the phrase "substantially the same" means that there is less than 2 N difference in flexibility (that is, flexure resistance force). In other embodiments, the second region 42 may have a higher flexure resistance force than the first region 40. In these or other embodiments, the absorbent member 20 may comprise one or more additional regions having different average densities relative to the first and second regions 40 and 42. These may comprise a third, fourth, fifth, etc. region.

2. Absorbent Members with "Regional De-Densification".

Figure 11:
FIG. 11 shows a web of dry lap after it has been processed according to another embodiment of the methods described herein in order to form an absorbent member with "regional de-densification".

FIG. 11 shows a web of dry lap after it has been processed according to another embodiment of the methods described herein in order to form an absorbent member 20 with "regional de-densification".

In embodiments of absorbent members with "regional de-densification", the portion 46 of the absorbent member 20 that is not de-densified may have a density similar to that of the precursor material 10. Thus, in such embodiments, the absorbent member 20 comprises at least two regions extending in the X and Y directions. These regions comprise: a) a first region having a density profile through its thickness that comprises a portion of the area of the absorbent member, and b) a second region comprising another portion of the area of the absorbent member. The first region 44 has a maximum density, wherein the mean maximum density measurement through the thickness of the absorbent member 20 is at least about 1.2 up to about 6.5, or more, times its mean minimum density. The second region 46 of the absorbent member has a mean maximum density measurement through the thickness is less than 1.2 times its mean minimum density, and may have a density similar to that of the precursor material.

G. Alternative Embodiments and Combinations

Figure 12:
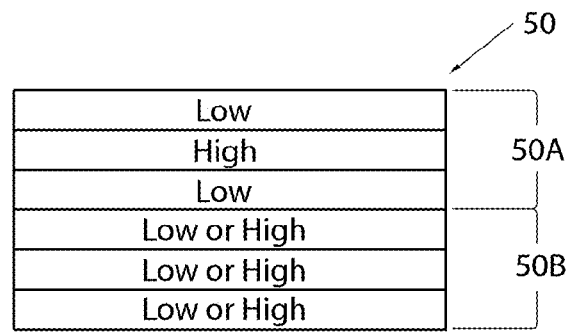
FIG. 12 is a schematic side view showing various embodiments of an absorbent structure comprising a first absorbent member that has a density profile through its thickness comprising a relatively higher density zone disposed in the Z-direction between two relatively lower density outer portions of the layer, and that comprises a second absorbent member adjacent to one surface of the first absorbent member.
Figure 13:
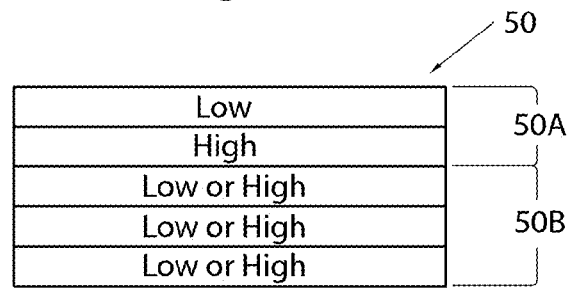
FIG. 13 is a schematic side view showing various embodiments of an absorbent structure comprising a first absorbent member that has a density profile through its thickness comprising a relatively lower density outer portion of the layer disposed in the Z-direction adjacent to a relatively higher density zone, and that comprises a second absorbent member adjacent to one surface of the first absorbent member.

Numerous non-limiting examples of alternative embodiments of the absorbent members described herein are possible. The embodiments of the absorbent members can be formed into numerous different types or combinations of absorbent structures. For example, as shown in FIG. 12, in one embodiment, an absorbent structure 50 can be made that comprises a second absorbent member 50B adjacent to one surface of a first absorbent member 50A, in which the first absorbent member 50A comprises an absorbent layer that has a density profile through its thickness comprising a relatively higher density zone (labeled "High" or "H") disposed in the Z-direction between two relatively lower density outer portions (labeled "Low" or "Lo") of the layer. As shown in FIG. 13, in another embodiment, an absorbent structure 50 can be made that comprises a second absorbent member 50B adjacent to one surface of a first absorbent member 50A, in which the first absorbent member 50A comprises an absorbent layer that has a density profile through its thickness comprising a relatively higher density zone disposed in the Z-direction adjacent to a relatively lower density outer portion of the layer. Numerous other absorbent structures are possible. Several possible variations of the arrangements of such higher density, H, and lower density, Lo, zones are shown in FIGS. 12 and 13. These structures may also comprise regions of apertures, protrusions, depressions or regions with different average densities that can extend through one or more of the absorbent members 50A and 50B.

II. Methods for Making the Absorbent Members

The methods of forming the absorbent members involve subjecting the precursor web to at least one cycle or pass through a mechanical deformation process.

The mechanical deformation process can be carried out on any suitable apparatus that may comprise any suitable type(s) of forming structures. Suitable types of forming structures include, but are not limited to: a pair of rolls that define a nip therebetween; pairs of plates; belts, etc. Using an apparatus with rolls can be beneficial in the case of continuous processes, particularly those in which the speed of the process is of interest. Although the apparatuses will be described herein for convenience primarily in terms of rolls, it should be understood that the description will be applicable to forming structures that have any other configurations.

The rolls used in the apparatuses and methods described herein are typically generally cylindrical. The term "generally cylindrical", as used herein, encompasses rolls that are not only perfectly cylindrical, but also cylindrical rolls that may have elements on their surface. The term "generally cylindrical" also includes rolls that may have a step-down in diameter, such as on the surface of the roll near the ends of the roll, and rolls that are crowned. The rolls are also typically substantially non-deformable. The term "substantially non-deformable", as used herein, refers to rolls having surfaces (and any elements thereon) that typically do not deform or compress when used in carrying out the processes described herein. The rolls can be made from any suitable materials including, but not limited to steel or aluminum. The steel may be made of corrosion resistant and wear resistant steel, such as stainless steel.

Figure 14:
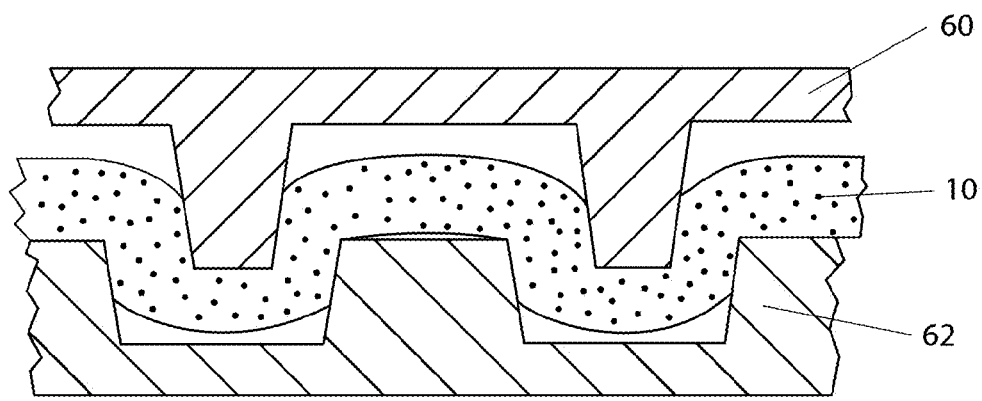
FIG. 14 is a cross-sectional side view of two embossing members in a prior art embossing process.
Figure 15:
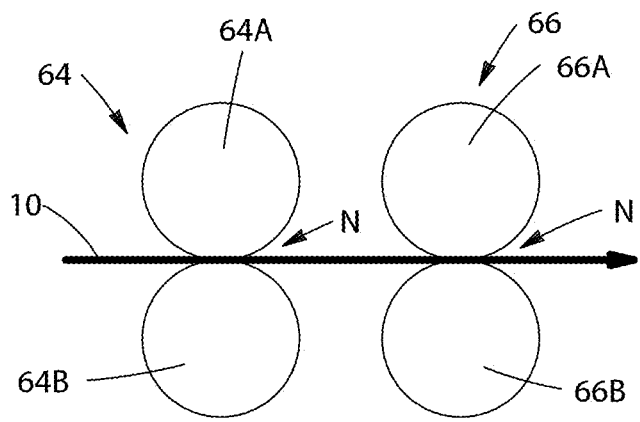
FIG. 15 is a schematic side view of one embodiment of an apparatus for making an absorbent member, such as a two side de-densified absorbent member shown in FIG. 2.

The components of the forming structure (for instance, the rolls of a pair of rolls) such as those shown in FIG. 15, may have any suitable type of surface. The surface of the individual rolls may, depending on the desired type of mechanical deformation, be: substantially smooth (i.e., an anvil roll) or provided with forming elements comprising protrusions or "male" elements. For rolls comprising ridges and grooves, the ridges are considered to be male forming elements. Male elements may be discrete (such as SELF teeth, RKA teeth, or pins) or continuous (such as the ridges on a ring roll). In some embodiments, the components of the forming structure may be substantially free of, or completely free of combinations of discrete male 60 and mating discrete female 62 elements such as those shown in FIG. 14 that would be used for embossing. The surfaces with the forming elements may have any suitable configuration. Suitable configurations for the forming elements include, but are not limited to: ring rolls; SELF rolls; Micro-SELF rolls; RKA rolls and pin rolls.

The forming elements on the SELF rolls can be oriented in either the machine direction (MD) or the cross-machine direction (CD). In certain embodiments, the SELF rolls comprise a plurality of alternating circumferential ridges and grooves around the circumference of the roll. The ridges have spaced apart channels formed therein that are oriented parallel to the axis A of the roll. The channels form breaks in the ridges that create forming elements or teeth on the SELF roll. In such embodiments, the teeth have their longer dimension oriented in the machine direction (MD). These roll configurations will be referred to herein as a standard "CD SELF" roll since the teeth are not staggered, and in the usual SELF process, the material being fed into a nip formed by such a roll would be stretched in the cross-machine direction (or "CD").

In other embodiments, which are described in the SELF patents that are incorporated by reference herein, the SELF roll can comprise a machine direction, or "MD SELF" roll. Such a roll will have alternating ridges and grooves that are oriented parallel to the axis A of the roll. The ridges in such a roll have spaced apart channels formed therein that are oriented around the circumference of the roll. The channels form breaks in the ridges to form forming elements or teeth on the MD SELF roll. In the case of MD SELF rolls, the teeth have their longer dimension oriented in the cross-machine direction (CD).

Figure 32:
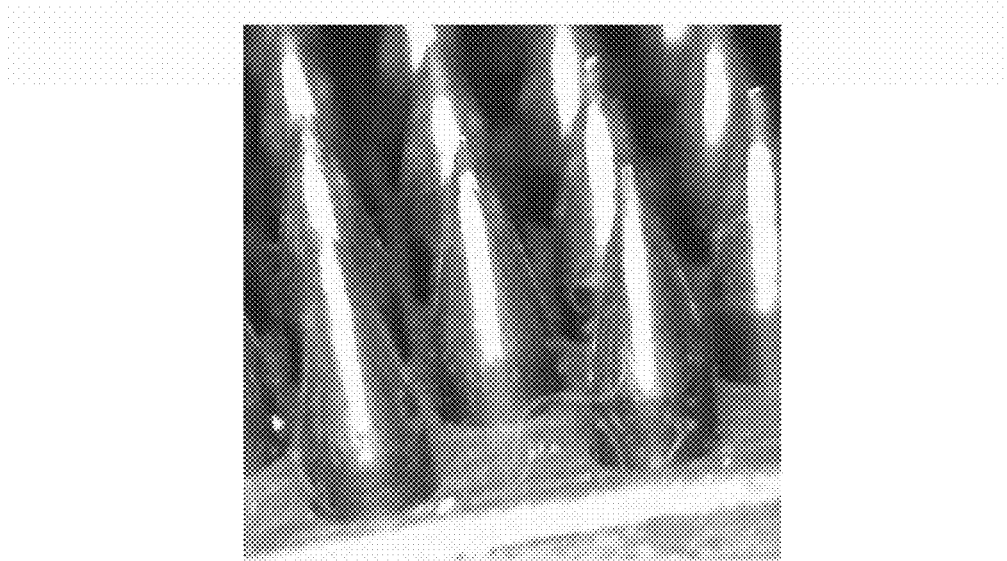
FIG. 32 shows a perspective view of the surface of another embodiment of a roll that can be used in the methods described herein.

FIG. 32 shows a portion of the surface of a roll having male elements of another configuration that can be used in the method. The roll shown in FIG. 32 is referred to herein as a "pin" roll. Unlike the previous tooth geometries described, the teeth of a pin roll are not faceted, meaning they do not comprise flat faces. The pin tooth can have various cross-sectional shapes, such as round or oval. The tip of the tooth can come to a sharp point, be rounded or be truncated so it has a flat surface. The tooth can also be bent at an angle. The side wall can taper from the base to tip at a constant angle, or the side wall can change angles. For example, the top of the tooth can have a cone-like shape with a 30 degree angle between the axis of the tooth and the side wall, and the base of the tooth can have a cylindrical shape with a vertical side wall that runs parallel to the axis of the tooth.

To form an absorbent structure which has a higher density portion on one side, at least one of the components of the forming structure (such as one of the rolls) may have a surface that is: smooth (such as a smooth anvil roll), substantially smooth, or relatively smooth. The phrase "relatively smooth surface", as used herein, means that the surface of the forming structure is not necessarily smooth, but is smoother than the surface of the other component of the forming structure. Thus, the phrase "relatively smooth surface" can, for example, include a ring rolling roll that is not smooth, but is "relatively" smoother than a SELF roll used as the other component of the forming structure. It should be understood that the phrase "relatively smooth surface" may include smooth and substantially smooth surfaces as well. The smoothness of the surface refers to the surface area of the forming elements that is capable of contacting a web. Thus, the larger the total area of the forming elements that is capable of contacting a web, the smoother the surface will be. To form an absorbent member which has a lower density portion on both sides, and a higher density region in between, both of the components of the forming structure (such as both of the rolls) should have forming elements on their surfaces. If it is desired to skew the density profile of the absorbent member, at least one of the components of the forming structure (such as one of the rolls) should have a relatively smooth surface. If it is desired to compact the absorbent member, the forming structures may comprise relatively smooth rolls as compared with those used to de-densify the web.

The rolls are non-contacting, and axially-driven. In cases where the rolls in a pair are patterned, the rolls may be meshing, non-meshing, or at least partially intermeshing. The term "meshing", as used herein, refers to arrangements when the forming elements on one of the components of the forming structure (e.g., roll) extend toward the surface of the other forming structure and the forming elements have portions that extend between and below an imaginary plane drawn though the tips of the forming elements on the surface of the other forming structure. The term "non-meshing", as used herein, refers to arrangements when the forming elements on one of the components of the forming structure (e.g., roll) extend toward the surface of the other forming structure, but do not have portions that extend below an imaginary plane drawn though the tips of the forming elements on the surface of the other forming structure. The term "partially intermeshing", as used herein, refers to arrangements when the forming elements on one of the components of the forming structure (e.g., roll) extend toward the surface of the other forming structure and some of the forming elements on the surface of the first roll have portions that extend between and below an imaginary plane drawn though the tips of the forming elements on the surface of the other forming structure, and some of the elements on the surface of the first roll do not extend below an imaginary plane drawn though the tips of the forming elements on the surface of the other forming structure.

The rolls in the pair of rolls will typically both rotate in opposite directions (that is, the rolls are counter-rotating). The rolls may rotate at substantially the same speed, or at different speeds. The phrase "substantially the same speed", as used herein, means that there is less than 0.3% difference in the speed. The speed of the rolls is measured in terms of surface or peripheral speed. The rolls may rotate at different surface speeds by rotating the rolls at different axial speeds, or by using rolls that have different diameters that rotate at the same axial speeds. The rolls may rotate at substantially the same speed as the speed at which the web is fed through the nip between the rolls; or, they may rotate at a greater or lesser speed than the speed at which the web is fed through the nip between the rolls. The faster roll may have a surface speed that is anywhere from 1.02 up to about 3 times faster than the slower roll. Suitable ranges for the surface speed ratio include between about 1.05 and about 2.0, depending on the geometry of the male elements. The greater the surface speed differential or ratio between the rolls, the greater the de-densification of the material.

The precursor web can be fed through the mechanical deformation process in any suitable orientation if the precursor web is in the form of sheets. If the precursor material is in the form of sheets, the individual sheets can be joined with their ends in an overlapping configuration by passing the sheets through a nip of an RKA or SELFing process. Typically, it will be fed into the mechanical deformation process in the machine direction if it is in roll form.

The precursor web can be fed through any suitable number of mechanical deformation processes. The number of mechanical deformation nips to which the precursor web is subjected can range from one to between 2 and 100, or more, nips.

A. Method for Making Two-Side De-Densified Absorbent Members

FIG. 15 shows one embodiment of an apparatus for making a two side de-densified absorbent member such as that shown in FIG. 2. The apparatus shown in FIG. 15 has two pairs of rolls 64 and 66 and may be referred to as a paired roll apparatus. Each pair of rolls comprises two rolls, 64A and 64B, and 66A and 66B, respectively, that forms a single nip N therebetween.

Figure 15A:
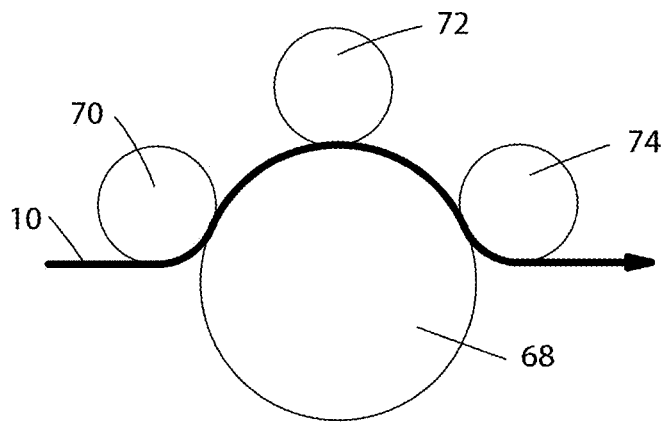
FIG. 15A is a schematic side view of another embodiment of an apparatus for making an absorbent member.
Figure 21:
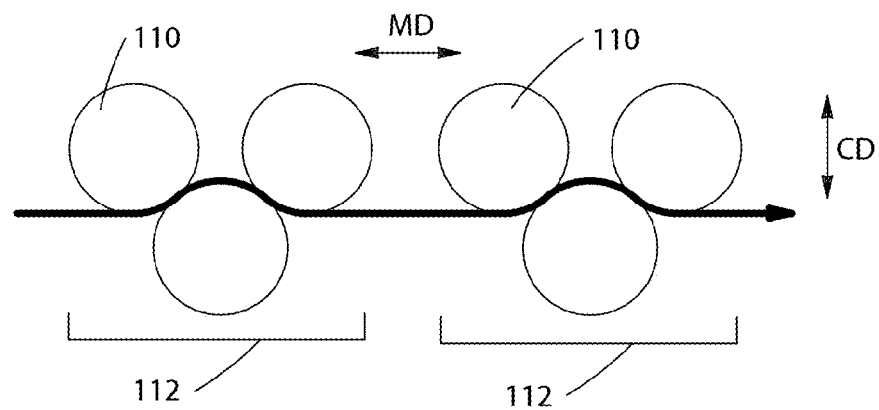
FIG. 21 is a schematic side view of another embodiment of an apparatus for making an absorbent member.

In the embodiment shown in FIG. 15, four rolls are shown; however, the apparatus can comprise any suitable number of rolls. The apparatus can, for example, have up to fifty, or more pairs of rolls. Multiple rolls are useful when it is desirable to run the precursor web 10 through multiple nips. In order to make the absorbent member 20 shown in FIG. 2, it may be desirable to run the precursor web 10 through as many as thirty or more nips. In order to run the precursor web 10 through thirty nips, if the rolls are arranged in a paired configuration, there would have to be thirty pairs of rolls. However, such roll arrangements are less than optimal since so many rolls are required, and the large number of rolls will occupy an excessive amount of space on a manufacturing floor. Therefore, applicants have developed improved configurations for arrangement of the rolls. The rolls can, depending on the embodiment, be arranged in any suitable configuration when viewed from the side, including: paired (FIG. 15); planetary configurations (FIG. 15A) with a central roll 68 and satellite rolls 70, 72, and 74; nested configurations (FIG. 15B); in the configuration of a closed loop (FIG. 15C); in configurations where the rolls are shared by two or more other rolls (which may be referred to as a "shared bank" (FIG. 15D); and combinations of such configurations (hybrid) (FIG. 21). These roll configurations are described in greater detail in U.S. patent application Ser. No. 13/094,206 filed on the same date as the present application, the disclosures of which are hereby incorporated by reference herein.

Figure 15B:
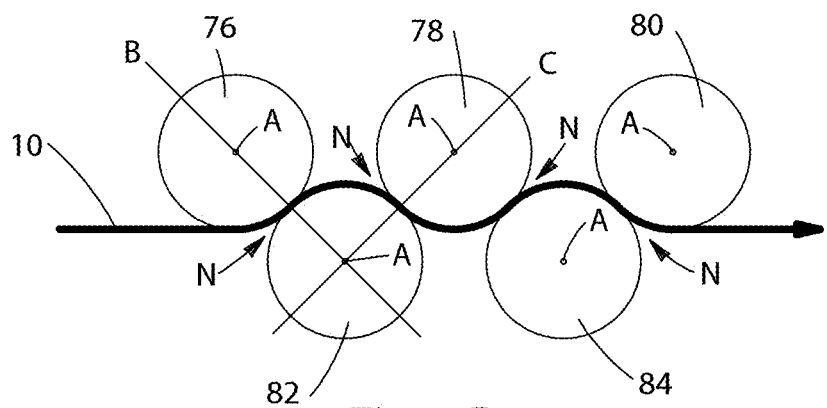
FIG. 15B is a schematic side view of another embodiment of an apparatus for making an absorbent member.
Figure 15C:
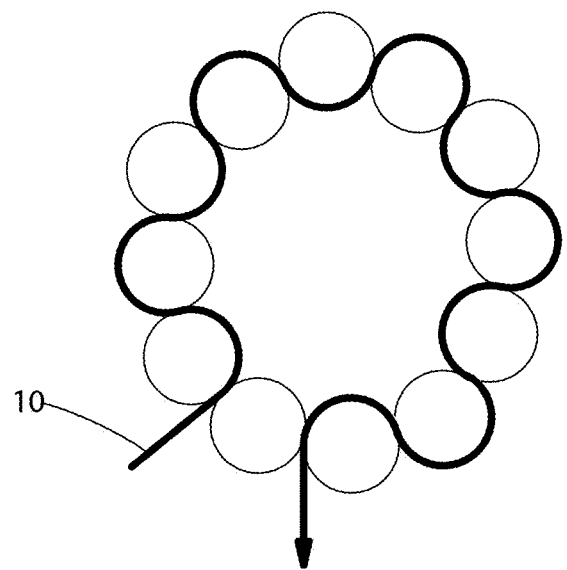
FIG. 15C is a schematic side view of another embodiment of an apparatus for making an absorbent member.
Figure 15D:
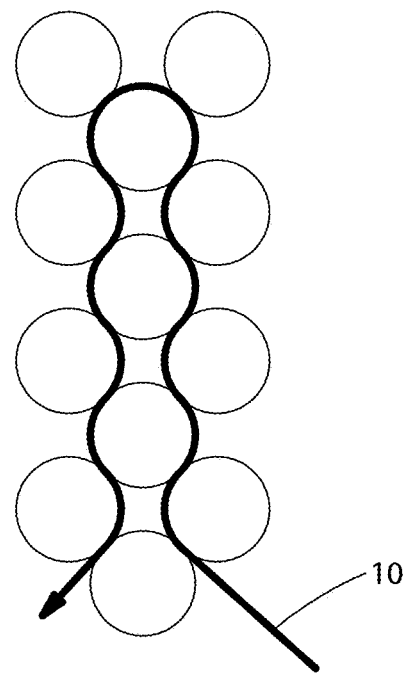
FIG. 15D is a schematic side view of another embodiment of an apparatus for making an absorbent member.

The apparatus shown in FIG. 15B will be referred to as a "nested roll" arrangement. In the nested roll apparatus, the rolls are arranged in an offset configuration when viewed from their sides (that is, their ends) in which one roll, such as rolls 78, 82, and 84, is positioned in a gap between two adjacent rolls so that at least two of the rolls define two or more nips N thereon with other rolls. Typically, in a nested roll arrangement, there will be at least four generally cylindrical rolls. More specifically, in a nested configuration, the rolls each have an axis, A, and the rolls are arranged so that if the rolls are viewed from one of their circular sides, and lines, such as B and C, are drawn through the axes A of at least two different pairs of said rolls (which pairs may have at least one roll in common), will be non-linear. As shown in FIG. 15B, at least some of the lines B and C drawn through the axes of adjacent pairs of rolls form an angle therebetween.

The nested roll arrangement may provide several advantages. A nested roll arrangement may provide more nips per total number of rolls than non-nested roll arrangements. This results in the need for substantially less tooling (machining of rolls) than in the paired roll apparatus. The nested roll arrangement maintains control of the web for registering deformations in the web since all portions of the web remain in contact with at least one of the rolls from the point where the web enters the first nip to the location where the web exits the last nip. The nested roll arrangement also has a smaller footprint on a manufacturing floor. The entire nested roll arrangement shown in FIG. 15B could also be rotated 90° so that the rolls are stacked vertically, and the apparatus would occupy even less space on a manufacturing floor.

Figure 16:
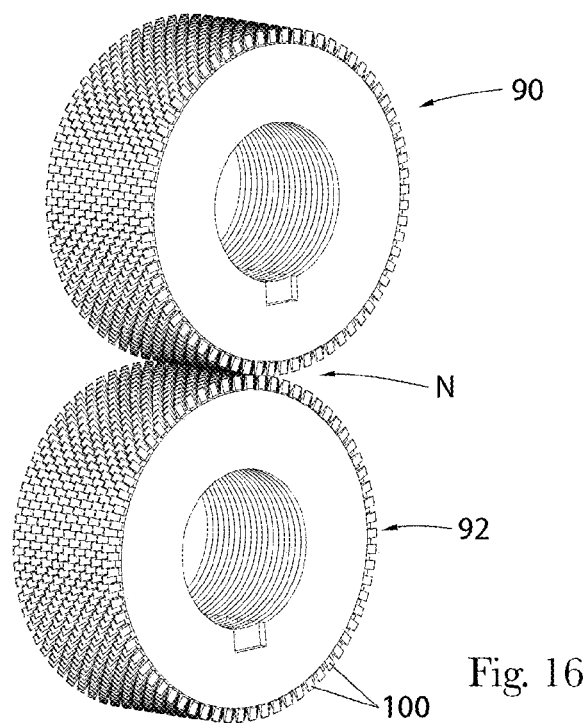
FIG. 16 is an enlarged perspective view of one non-limiting embodiment of the surfaces of two of the rolls in the apparatus.

FIG. 16 is a close up of one non-limiting embodiment of the surfaces of two of the rolls 90 and 92 in the apparatus. The rolls 90 and 92 are carried on respective rotatable shafts (not shown) having their axes of rotation disposed in a parallel relationship. In this embodiment, each of the rolls 90 and 92 comprises a variation of one of the Procter & Gamble Company's SELF technology rolls. In this embodiment, the forming elements (or teeth) 100 on the SELF rolls have their longer dimension oriented in the machine direction (MD).

As shown in FIG. 16, the surfaces of the rolls each have a plurality of spaced apart teeth 100. The teeth 100 are arranged in a staggered pattern, which is shown in greater detail in FIG. 17. More specifically, the teeth 100 are arranged in a plurality of circumferentially-extending, axially-spaced rows, such as 102A and 102B, around the roll. But for the spacing TD between the teeth in each row, the teeth in each roll would form a plurality of circumferentially-extending, axially-spaced alternating ridges and grooved regions. The tooth length TL and machine direction (MD) spacing TD can be defined such that the teeth in adjacent rows 102A and 102B either overlap or do not appear to overlap when the rolls are viewed from one of their ends. In the embodiment shown, the teeth 100 in adjacent rows are circumferentially offset by a distance of 0.5x (where "x" is equal to the tooth length plus the MD spacing TD between teeth in a given row). In other words, the leading edges LE of adjacent teeth in adjacent rows will be offset in the MD by 0.5x. The rolls 90 and 92 are aligned so that the rows of teeth in one roll align with the grooved regions between the teeth in the other roll. The staggered tooth pattern allows the precursor web 10 to be mechanically impacted relatively uniformly while avoiding the need to time or phase the rolls in the machine direction. The rolls shown in FIG. 16 can be made in any suitable manner, such as by first cutting the ridges and grooves into the roll, then helically cutting the teeth 100 into the surface of the rolls with each cut being continuous. If desired, the tooth profile (in particular, the leading and trailing edges) can be modified by using a plunge cut.

Figure 17:
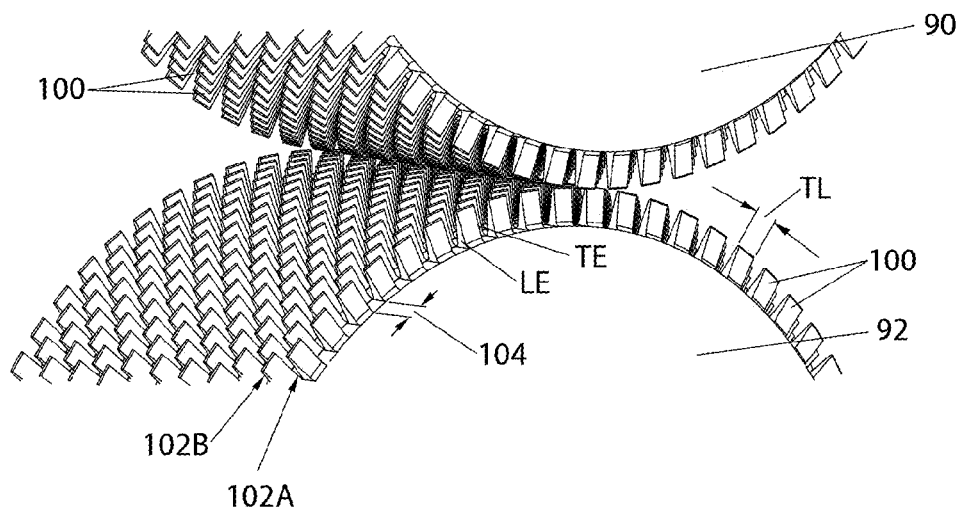
FIG. 17 is a further enlarged perspective view of the surfaces of the rolls shown in FIG. 16.
Figure 18:
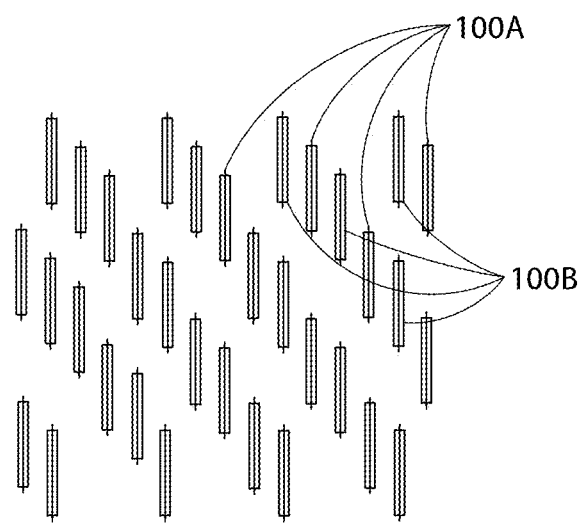
FIG. 18 is a schematic plan view of an area on a web showing how the teeth on the two rolls could align in the nip.

The roll configuration shown in FIGS. 16 and 17 will be referred to herein as a "staggered CD SELF" roll since in the usual SELF process, the material being fed into the nip N between such rolls would be stretched in the cross-machine direction (or "CD"). The advantage of using CD SELF rolls in the methods described herein is that registration of multiple rolls to provide multiple hits (impacts within nips) is much easier in that it is only necessary to register the toothed regions (that is, to align the toothed regions with the grooved regions on the opposing roll) in the cross-machine direction, and it is not necessary to phase or register the toothed regions in the MD). FIG. 18 is a schematic plan view of an area on a web showing an example of how the teeth on the two rolls could align in the nip. FIG. 18 shows the areas 100A impacted on a web by teeth on roll 90 and areas 100B impacted by the teeth on roll 92.

Figure 19:
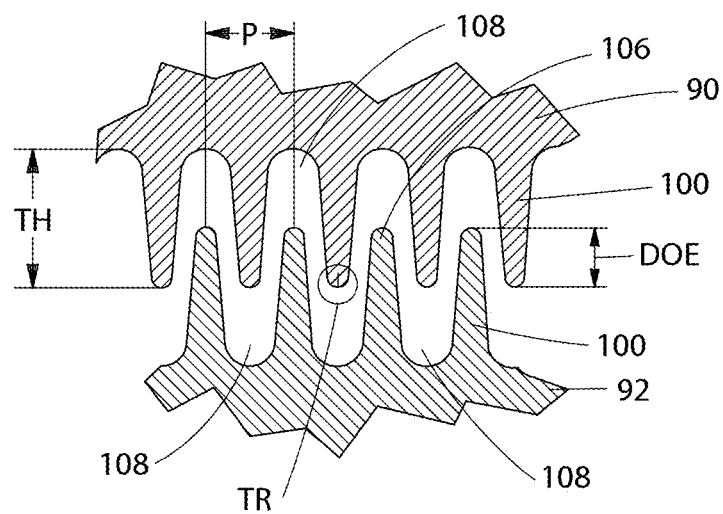
FIG. 19 is a cross-section of a portion of the intermeshing rolls.

FIG. 19 shows in cross section a portion of the intermeshing rolls 90 and 92 including teeth 100 which appear as ridges 106 and grooves 108 between the teeth 100. The teeth can have a triangular or inverted V-shape when viewed in cross-section. The vertices of teeth are outermost with respect to the surface of the rolls. As shown, teeth 100 that have a tooth height TH, a tooth length TL (FIG. 17), and a tooth-to-tooth spacing (or ridge-to-ridge spacing) referred to as the pitch P. The tooth length TL in such embodiments is a circumferential measurement. The outermost tips of the teeth have sides that are preferably rounded to avoid cuts or tears in the precursor material. The leading and trailing edges LE and TE (FIG. 17), respectively, of the teeth 100 are preferably square or a shape that creates a relatively sharp edge to maximize de-densification of the web in the process. As shown, the ridges 106 of one roll extend partially into the grooves 108 of the opposed roll to define a "depth of engagement" (DOE) E, which is a measure of the level of intermeshing of rolls 90 and 92. The depth of engagement can be zero, positive for meshing rolls, or negative for non-meshing rolls. The depth of engagement E, tooth height TH, tooth length TL, tooth spacing TD and pitch P can be varied as desired depending on the properties of precursor web 10 and the desired characteristics of the absorbent member 20. For example, in general, to obtain the greatest amount of de-densification in the fewest number of hits, while preserving a portion of the integrity of the web, it is preferred to have a short tooth length TL and a small tip radius TR to maximize the amount of bending around the tooth and minimize the amount of compression on the material. Thus, it may be desirable for the tooth tip radius TR to be less than 0.020 inch (about 0.5 mm). However, this must be balanced with the need to have a tooth that will not easily break when the force from the deformation is applied. The tooth spacing TD between the teeth should be large enough to enable the material to bend around the leading and trailing edges, LE and TE, respectively, of the teeth. If the TD is too small, the material will bridge the gap between the teeth and the amount of de-densification will be lower. The optimum pitch of the teeth 100 depends on the thickness of the precursor material 10, and is typically around two times the thickness of the web 10. If the pitch P is too small, the material 10 will remain fairly dense after multiple passes. If the pitch P is too high, the CD spacing between the teeth 100 after the rolls are mated together will be greater than the thickness of the web 10 and the teeth 100 will not sufficiently create shear between the layers of the web, which is required to selectively break the hydrogen bonds.

Figure 20:
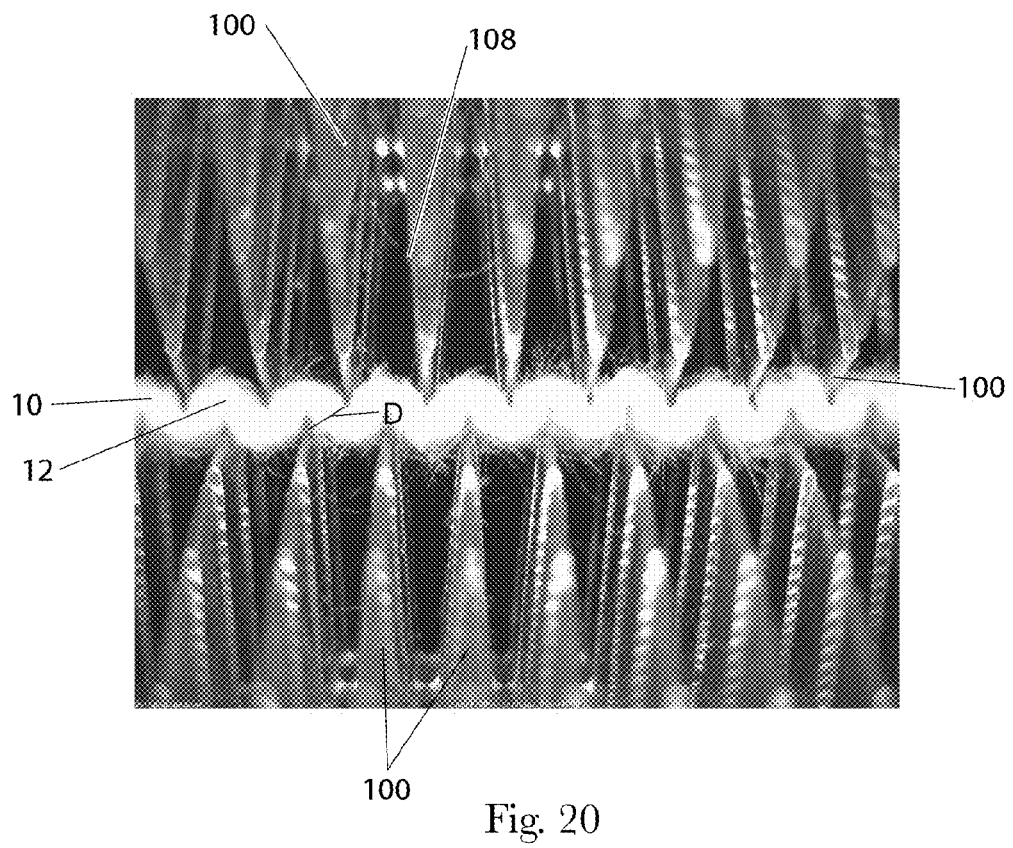
FIG. 20 is a photograph of a web between a portion of the intermeshing rolls.

FIG. 20 is an even further enlarged view of several inter-engaged teeth 100 and grooves 108 with a web 10 of material therebetween. As shown, a portion of a web 10, which can be precursor web such as shown in FIG. 1, is received between the inter-engaged teeth 100 and grooves 108 of the respective rolls. The inter-engagement of the teeth 100 and grooves 108 of the rolls causes laterally spaced portions 12 of web 10 to be pressed by teeth 100 into opposed grooves 108. In the course of passing between the forming rolls, the web bends around the teeth 100, inducing shear forces in the web that result in the selective breakage and preservation of hydrogen bonds and disentanglement of the fibers. As shown in FIG. 20, the teeth 100 do not penetrate through the thickness of the precursor web 10. (However, in other embodiments such as when the rolls are rotated at different speeds, the teeth may penetrate through the thickness of the precursor web 10.) The teeth described here has a smaller tip radius TR than male elements in typical embossing processes to ensure the amount of compaction of the material 10 is minimized as the material is being bent over the teeth 100. Also, unlike embossing, the clearance between the teeth, or the shortest distance D between the tips of the teeth 100 of the tooling described here, may be smaller than the thickness of the web 10 to induce additional shear forces in the web. This results in a greater amount of de-densification of the material because hydrogen bonds are not only broken on the outer surfaces of the web but also may be broken inward of the outer surfaces of the web. In addition, the forces of teeth 100 pressing web 10 into opposed grooves 108 impose within web 10 tensile stresses that act in the cross-web direction. The tensile stresses can cause intermediate web sections 12 that lie between and that span the spaces between the tips of adjacent teeth 100 to stretch or extend in a cross-web direction, which can also result in the breakage of hydrogen bonds between the fibers and the disentanglement of fibers. Tensile stresses are undesirable because they do not selectively break hydrogen bonds, rather the hydrogen bonds can be broken throughout the entire thickness of the web and in an uncontrolled manner. Therefore, unlike in prior applications of SELFing technology, the depth of engagement E of the rolls is kept low to minimize the tensile stresses put on the web 10. If the tensile stresses become too large, the web will become very weak, fracture and be difficult to process. It will also not perform as well in use because the continuity of the fibrous matrix is broken.

Because of the localized cross-web stretching of web 10 that has taken place, with the consequent increase in web width, the web material that exits from the forming rolls can have a lower basis weight than that of the entering web material, provided the exiting material remains in a substantially flat, laterally extended state. The resulting modified web can have a web width that can range from about 100% to about 150% of the initial web width and a basis weight that is less than or equal to the web's original basis weight.

For making an absorbent member 20 such as that shown in FIG. 2 from a precursor web having a basis weight in the range of from about 200 to 700 gsm, the teeth 100 may have a length TL ranging from about 0.5 mm (0.020 inch), or less, to about 10 mm (0.400 inch) and a spacing TD from about 0.5 mm (0.020 inch) to about 10 mm (0.400 inch), a tooth height TH ranging from about 0.5 mm (0.020 inch) to about 10 mm (0.400 inch), a tooth tip radius TR ranging from about 0.05 mm (0.002 inch) to about 0.5 mm (0.020 inch), and a pitch P between about 1 mm (0.040 inches) and 10 mm (0.400 inches). The depth of engagement E can be from about −1 mm (−0.040 inch) to about 5 mm (0.200 inch) (up to a maximum approaching the tooth height TH). Of course, E, P, TH, TD, TL, and TR can each be varied independently of each other to achieve the desired properties in the absorbent member. In one embodiment of roll useful for making an absorbent member such as that shown in FIG. 2, teeth 100 have a uniform circumferential length dimension TL of about 0.080 inch (2 mm) measured generally from the leading edge LE to the trailing edge TE, a tooth tip radius TR at the tooth tip of about 0.005 inch (0.13 mm), are uniformly spaced from one another circumferentially by a distance TD of about 0.080 inch (2 mm), have a tooth height TH of 0.138 inch (3.5 mm), have a tooth side wall angle of about 8.5 degrees (measured from the base of the tooth to near the tip of the tooth, before the formation of the radius), and a have a pitch of about 0.080 inch (2 mm). The clearance between the teeth of mating rolls linearly varies with the depth of engagement. For this embodiment, the clearance of the teeth for non-meshing rolls at −0.010 inch (0.25 mm) depth of engagement is 0.034 inch (0.86 mm) and the clearance for meshing rolls at 0.015 inch (0.38 mm) depth of engagement is 0.029 inch (0.74 mm).

The process used herein differs from Procter & Gamble's SELF process in a number of respects. One distinction is that the web materials described herein will typically not be formed into structures provided with rib-like elements and elastic-like properties. Rather, the SELF process is used in the present context to mechanically deform the precursor web material 10 and induce shear forces in localized areas 12 between the teeth 100 of the forming structures in order to flex the web 10 and selectively break hydrogen bonds to reduce the density and increase the flexibility of the precursor web material. Another distinction is that, in the case of some roll configurations used herein, the thickness of the web may be substantially greater than the DOE in the present process.

Previously, it was believed that a DOE less than the thickness of the web 10 would not be effective. However, in the processes described herein, the DOE may be negative or less than the thickness of the web. (Although in the case of some roll configurations, such as pin rolls, the depth of engagement may be greater than the thickness of the web because such forming elements provide more clearance between adjacent elements, and a higher DOE is needed for the desired shear and bending of the precursor web by such elements.) The first two examples in the table below represent typical settings for prior SELFing applications, showing the ratio of thickness to DOE is typically much less than 1. The third and fourth examples in the table below represent examples of settings for the current processes, showing the ratio of thickness to DOE is typically equal or greater than 1. For negative DOE values, the ratio of thickness to DOE is obtained by dividing the thickness by the absolute value of the DOE.

| Material | Material Thickness (inches/mm) | DOE (inches/mm) | Ratio of Thickness to DOE |
| --- | --- | --- | --- |
| PE film | 0.001/0.025 | 0.040/1.0 | 0.025 |
| Spunbond nonwoven | 0.020/0.51 | 0.090/2.3 | 0.22 |
| Drylap 200 gsm | 0.020/0.51 | 0.015/0.38 | 1.3 |
| Drylap 680 gsm | 0.060/1.5 | 0.001/0.025 | 60 |

Numerous variations of the process described herein are possible. The processes described herein can be configured and controlled to locally bend the precursor material 10 in opposite directions in the same location across the surface of the web when the web passes from one nip to another. The apparatus can also be configured and controlled to locally bend the precursor material 10 in different locations across the surface of the web when the web passes from one nip to another. It is desirable for the rolls to be patterned and arranged such that the precursor material is deformed in the greatest number of different locations on the surface before exiting the process, and so that this is accomplished in the fewest number of hits and/or in the smallest process footprint. The rolls can have staggered or standard patterns. The rolls can be aligned or mis-aligned relative to each other in the MD and/or CD. The rolls may all have the same SELF pattern thereon, or the pattern on the rolls and/or DOE can vary between rolls (that is, for each pass through a nip). The desired DOE for each pass depends on caliper of the precursor material at each pass. An example of an apparatus that maximizes the de-densification of the material 10 in a small process footprint is shown in FIG. 21. As shown in FIG. 21, the apparatus includes rolls 100 with staggered patterns arranged in a hybrid arrangement such that there are multiple three to four nested roll clusters 112 that are then off-set relative to each other in the CD.

The apparatus for de-densifying the precursor material can be provided at any suitable location, or stage, in the process of manufacturing an absorbent article. In some embodiments, the method can serve as a pre-processing step prior to feeding the precursor material into a hammer mill in order to reduce the energy required to defibrillate the material in the hammer mill. In other embodiments, the method and apparatus can be provided instead of a hammer mill at a location apart from an absorbent article manufacturing line, such as at the location formerly occupied by the hammer mill. In still other embodiments, instead of being in a separate location from the absorbent article manufacturing line, the apparatus for de-densifying dry lap can be located as a unit operation at or near the beginning (or at some other convenient location) of an absorbent article manufacturing line in order to prepare a completed absorbent member that is ready for use in an absorbent article being made on the line.

It may be desirable to make the width of the roll of precursor material equal to the width or length of the absorbent core, or other structure desired to be formed so that the roll of absorbent member material can be conveniently cut into individual cores.

The process described above, thus, may use an apparatus that has male elements on opposing surfaces in contrast to embossing apparatuses that employ male elements on one surface and female elements within which the male elements fit, on an opposing surface. In addition, in the present process, the clearance between the elements may be less than the thickness of the web. This may be used to apply increased shear forces on the web (in contrast to apparatuses that require that the clearance between elements be greater than or equal to that of the web being processed). The process described herein may be capable of not only breaking weak hydrogen bonds on the surface of the precursor material to soften the surface of the same, it may also selectively break the stronger hydrogen bonds and those bonds towards the interior of the material and significantly de-densify and weaken the web. It can also be used to significantly increase the caliper (measured under load) of the precursor web. The structure of precursor web can be preserved in certain zones for strength while hydrogen bonds can be broken in other zones for acquisition.

B. Method for Making One-Side De-Densified Absorbent Members

In the methods for making one-side de-densified absorbent members, the precursor web 10 is subjected to multiple passes through a nip formed between rolls having discrete forming elements thereon and opposing rolls that have a relatively smoother surface pattern.

Figure 22:
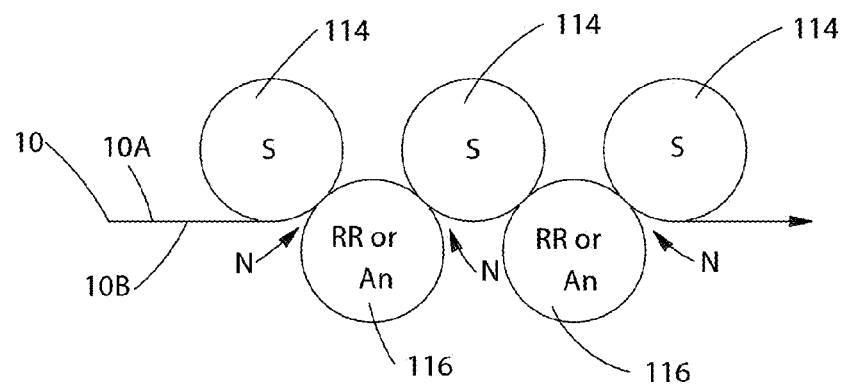
FIG. 22 is a schematic side view of one embodiment of an apparatus for making an absorbent member, such as a one side de-densified absorbent member shown in FIG. 5.

FIG. 22 shows an embodiment of an apparatus for making a one side de-densified absorbent member 20 such as that shown in FIG. 5. In this embodiment, the apparatus provides a plurality of nips N between rolls having forming elements thereon, and opposing rolls that have a relatively smoother surface pattern. FIG. 22 shows a nested roll apparatus in which the rolls 114 on a first side 10A of the precursor web 10 have forming elements thereon, and the rolls 116 on the second side 10B of the precursor web 10 have a relatively smoother surface pattern. In the embodiment shown, each roll 116 having a relatively smoother surface pattern forms a nip N with two rolls 114 having forming elements thereon.

In such an embodiment, the rolls 114 having forming elements thereon can comprise any suitable type of roll having discrete forming elements thereon including, but not limited to any of the configurations of SELF rolls and RKA rolls described above in conjunction with the method of making the two-side de-densified absorbent members.

The rolls 116 with the relatively smooth surface can comprise any suitable type of roll having a smoother surface than that of the roll having forming elements thereon. The rolls 116 with the relatively smooth surface include, but are not limited to: flat anvil rolls, ring rolls (in which the ridges and grooves are either MD or CD oriented); or, another SELF roll of the same or different pattern than the roll having forming elements thereon. In cases in which the rolls 116 with the relatively smooth surface comprise either a ring roll or a SELF roll, such a roll could have elements thereon with a smaller pitch than the roll having forming elements thereon or with a larger tip radius. In cases in which the rolls 116 with the relatively smooth surface comprise a SELF roll, such a roll could have elements thereon with longer teeth and/or smaller MD spacing between the teeth to make them more like ring rolls.

In two non-limiting examples, the nip N could be formed by either a SELF roll and a flat anvil roll, or a SELF roll and a ring roll. The combination of a SELF roll and a flat anvil results in less overall de-densification, higher interior maximum density, and higher exterior density of the surface of the precursor web that is passed through the nip N against the anvil roll. The combination of a SELF roll and a smaller pitch ring roll will result in a shift in the location of the maximum interior density in the absorbent member 20, but the maximum interior density will be lower and both exterior surfaces of the absorbent member 20 will be more highly de-densified (in comparison to the combination of a SELF roll and an anvil roll).

In this method, the forming elements on said first forming member, rolls 114 having forming elements thereon penetrate into the first surface 10A of said precursor web material 10 only part of the way into the thickness of the precursor web material, and the second surface 10B of said precursor web material is in contact with the surface of the second roll, rolls 116 with the relatively smooth surface.

C. Method for Making Re-Densified/Compacted Absorbent Members

The method of making a re-densified/compacted absorbent member involves first de-densifying a precursor web material 10 using one of the approaches described above for forming either the two-side or one-side de-densified absorbent members. The de-densified absorbent material is then compacted. The de-densified absorbent material can be compacted in any suitable manner. The de-densified absorbent material can be compacted over its entire surface, or in select areas/regions in the x-y plane.

Figure 23:
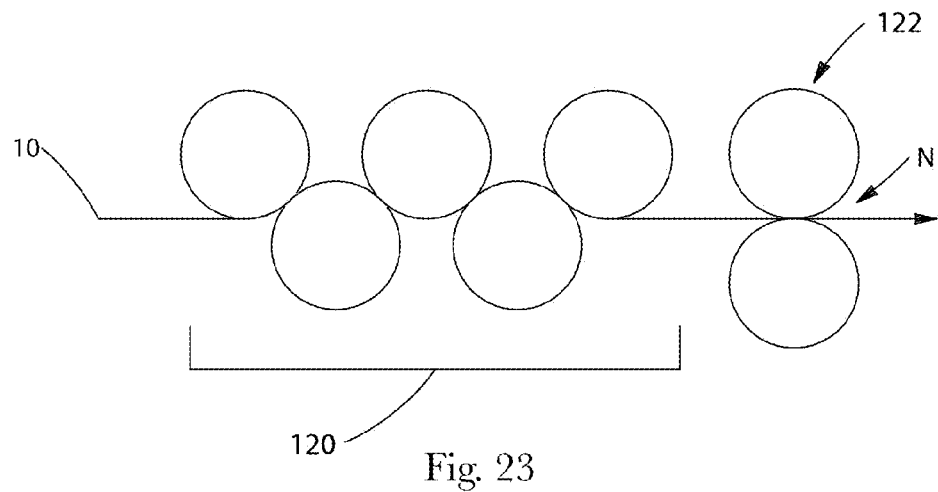
FIG. 23 is a schematic side view of one non-limiting embodiment of an apparatus for making a re-densified/compacted absorbent member such as that shown in FIG. 7, or a three-dimensional or apertured absorbent member such as shown in FIGS. 8 and 9, respectively.

FIG. 23 shows one non-limiting embodiment of an apparatus for making a re-densified/compacted absorbent member 20 such as that shown in FIG. 7. As shown in FIG. 23, the apparatus may comprise a nested roll arrangement 120 similar to that shown in FIG. 15B or FIG. 22. After the precursor web 10 passes through the nested roll arrangement 120, it is then fed through an additional compacting station 122, which may comprise a pair of rolls that form a nip therebetween. Options for the forming structures in this compacting station 122 include the following combinations: flat anvil on flat anvil (in order to compact all over); patterned roll on flat anvil (to compact select areas); or patterned roll on patterned roll (in order to compact select areas). In the densifying/compacting process, the patterned roll (such as ring roll) should have regions that are relatively smoother than the surfaces of the forming members used in the de-densifying step.

D. Method for Making Three Dimensional Absorbent Members

The method of making a three dimensional absorbent member involves subjecting the precursor web to a process for forming a three dimensional structure into the precursor web before and/or after it is de-densified such as described in sections IIA or B above. The method of making a three dimensional absorbent member, thus, may involve first de-densifying a precursor web material, such as by using one of apparatuses described above for forming either the two-side and one-side de-densified structures. The de-densified absorbent material is then subjected to a further mechanical deformation step using forming members having forming elements thereon that have a greater MD and/or CD spacing therebetween than the forming elements used in the prior steps and a greater depth of engagement. The de-densified absorbent material can be subjected to a further mechanical deformation step in any suitable manner. Alternatively, the precursor web material could first be subjected to a mechanical deformation step using forming members having forming elements thereon that have a greater MD and/or CD spacing therebetween and a greater depth of engagement and then de-densified using one of the approaches described above.

Figure 24:
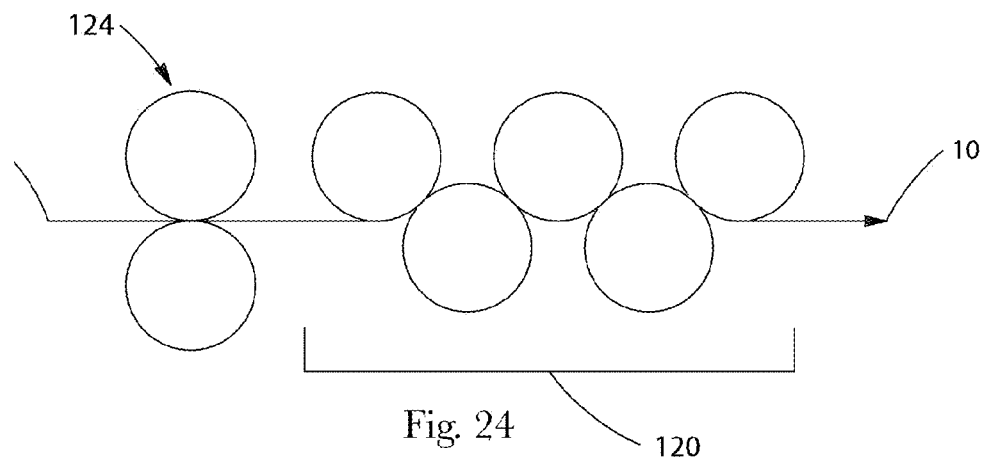
FIG. 24 is a schematic side view of one non-limiting embodiment of an apparatus for making a three-dimensional or apertured absorbent member such as shown in FIGS. 8 and 9, respectively.

FIG. 24 shows one non-limiting embodiment of an apparatus for making a three-dimensional absorbent member such as those shown in FIG. 8. As shown in FIG. 24, the apparatus may comprise a nested roll arrangement 120 similar to that shown in FIG. 15B or FIG. 22. Before the precursor web 10 passes through the nested roll arrangement 120, it is fed through an initial three-dimensional forming station 124, which may comprise a pair of rolls that form a nip therebetween. In alternative embodiments, the precursor web 10 can be passed through the nested roll arrangement 120, and then fed through a three-dimensional forming station 124. An apparatus for carrying out this later process would be similar to the apparatus shown in FIG. 23 where the compacting station 122 is replaced with a three-dimensional forming station 124.

The three-dimensional forming station 124 can comprise any suitable combination of forming members that are capable of imparting a three-dimensional texture to the precursor web 10. At least one of the forming members, which will be referred to as the three-dimensional forming member, should have male elements thereon having a pitch that is greater than the pitch of the elements used for de-densification. Several examples of three-dimensional forming rolls are described below. The direction of the ridges or teeth on the opposing roll should be the same as that on the three-dimensional forming roll. The depth of engagement of the elements on the three-dimensional forming roll with the forming elements on the opposing roll is typically at least 0.04 inch (1 mm). Any roll satisfying the above requirements can be used as the opposing roll. The opposing roll can, for example, be either a ring roll or a SELF roll.

Figure 25:
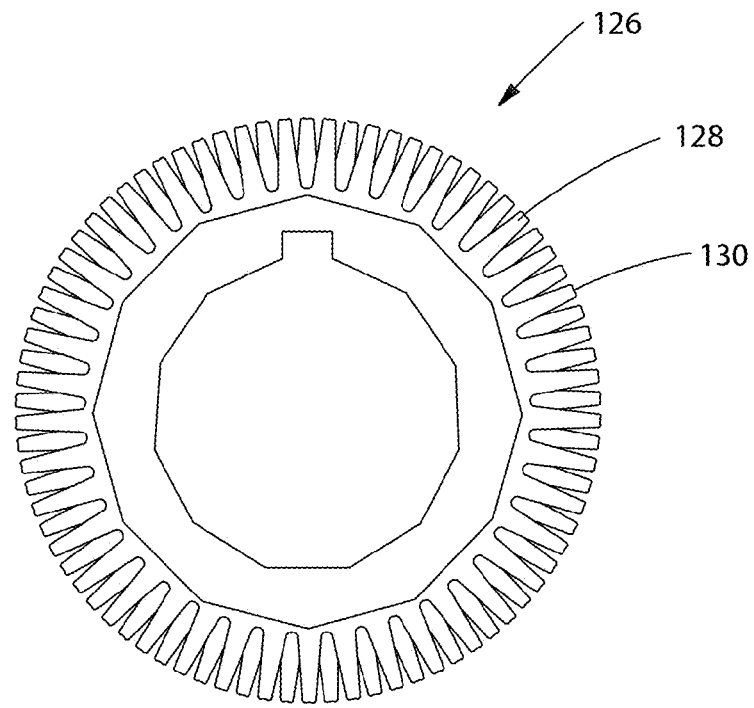
FIG. 25 is a schematic side view of one non-limiting example of a forming member for the step of forming the precursor web into a three dimensional absorbent member.
Figure 26:
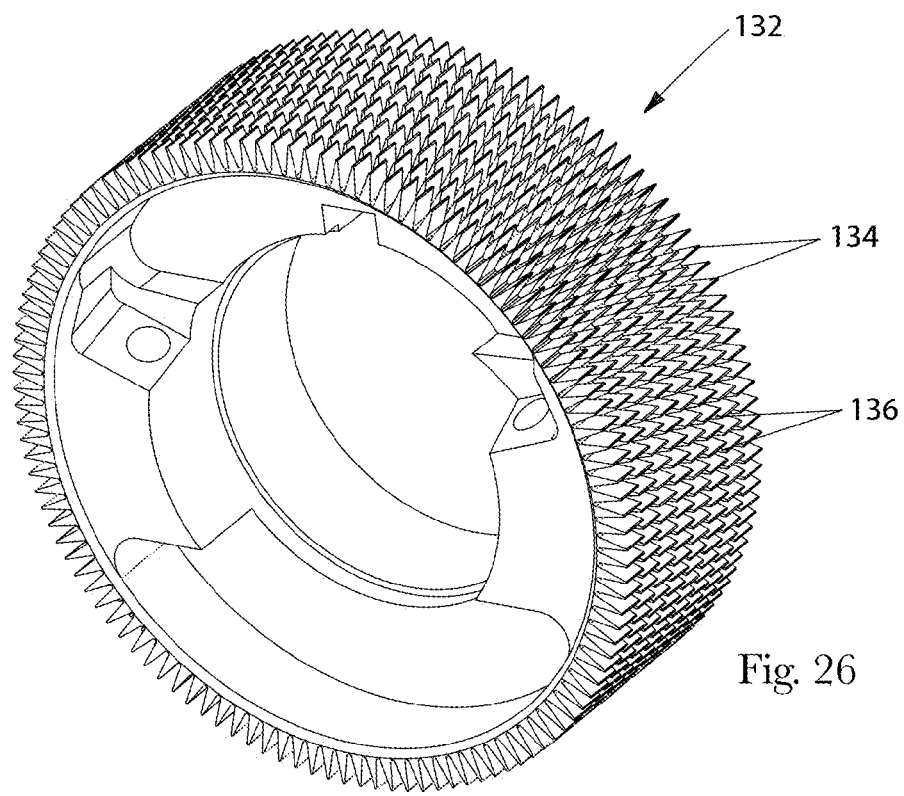
FIG. 26 is a perspective view of another example of a forming member for the step of forming the precursor web into a three dimensional absorbent member.

FIG. 25 shows one non-limiting example of a three dimensional forming roll 126 for the step of forming the precursor web 10 into a three dimensional absorbent member. As shown in FIG. 25, the forming roll 126 comprises a larger pitch CD SELF roll in which the teeth 128 are oriented in the machine direction, and are staggered. In the embodiment shown in FIG. 25, the tips 130 of the teeth 128 are concave. FIG. 26 shows another example of a forming member 132 for the step of forming the precursor web 10 into a three dimensional absorbent member. As shown in FIG. 26, the forming member 132 comprises an MD SELF roll in which the teeth 134 are oriented in the CD and are staggered. The roll 132 has spaced apart channels 136 formed therein that are oriented around the circumference of the roll. Examples of suitable forming element (or tooth) dimensions and DOEs for the rolls shown in FIGS. 25 and 26 are provided below. The forming elements on the opposing ring roll or SELF roll may have the same pitch as the rolls described below.

|  | Large Pitch SELF | MD SELF |
| --- | --- | --- |
| Pattern | Staggered | Staggered |
| Pitch | 200 | 185 |
| Tooth length | 0.118 in. (3 mm) | 0.250 in. (6.4 mm) |
| Tooth spacing | 0.328 in. (8.3 mm) | 0.250 in. (6.4 mm) |
| Tip radius | 0.010 in. (0.25 mm) | 0.010 in. (0.25 mm) |
| Tip shape | Concave | Flat |
| DOE for 3D samples | 0.105 in. (2.7 mm) | 0.090 in. (2.3 mm) |

E. Method for Making Apertured Absorbent Members

The method of making an apertured absorbent member involves aperturing a precursor web material before and/or after de-densifying the precursor web material, such as by using one of approaches described above for forming the two-side and one-side de-densified structures. The apparatus for making an apertured absorbent member may, thus, utilize a roll arrangement similar to that shown in FIG. 23 or 24, for example. However, the additional station or nip will comprise an aperturing forming member.

The precursor web 10 can be apertured in any suitable manner. Any aperturing processes known in the art can be used including, but not limited to: RKA rolls, or (high DOE) SELF rolls in which the DOE is greater than thickness of web to create apertures. The precursor web 10 can be apertured over its entire surface or in regions.

Figure 27:
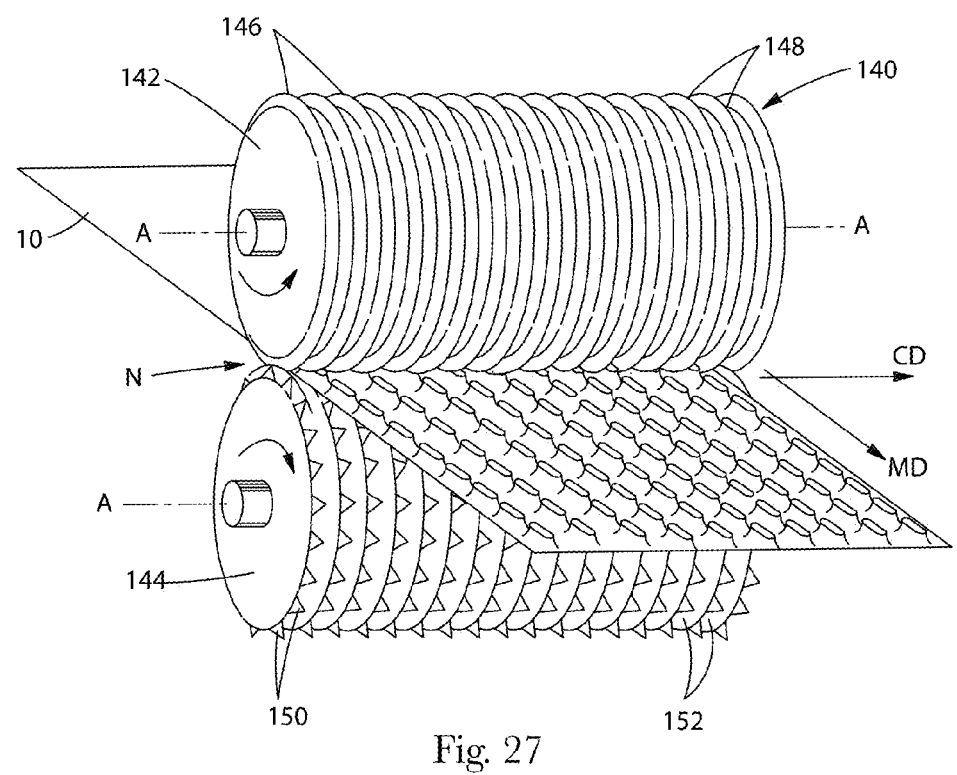
FIG. 27 is a schematic side view of one non-limiting example of a forming member for the step of forming the precursor web into an apertured absorbent member.

FIG. 27 shows one non-limiting example of an aperturing station 140 for the step of forming the precursor web 10 into an apertured absorbent member. As shown in FIG. 27, aperturing station 140 comprises a pair of counter-rotating, intermeshing rollers, wherein the top roll 142 is a ring roll, and the bottom roll 144 is a Rotary Knife Aperturing (or "RKA") roll. As shown in FIG. 27, the top ring roll 142 comprises circumferentially-extending ridges 146 and grooves 148. The bottom roll 144 comprises circumferentially-extending alternating rows of teeth 150 and grooves 152. The teeth 150 are joined to the bottom roll at their bases. The teeth 150 are tapered from their base to their tip, and the base of the teeth have a cross-sectional length dimension greater than a cross-sectional width dimension. Typically, apertures are formed in the web material 10 as the teeth on the RKA roll intermesh with grooves on the ring roll 142. RKA rolls are described in greater detail in U.S. Patent Application Publication No. US 2006/0087053 A1.

F. Method for Making Absorbent Members Having X-Y Regions with Different Densities 1. Entire Absorbent Member has Density Profile.

In some embodiments, the entire absorbent member may have a density profile, and the absorbent member may have different regions in the X-Y plane with different densities and/or different density profiles. One method of making an absorbent member having X-Y regions with different densities and/or density profiles is similar to the method of making a re-densified/compacted absorbent member. In order to make an absorbent member having X-Y regions with different densities, after de-densifying the absorbent material, the de-densified absorbent material is compacted only in select areas/regions in the x-y plane.

Figure 28:
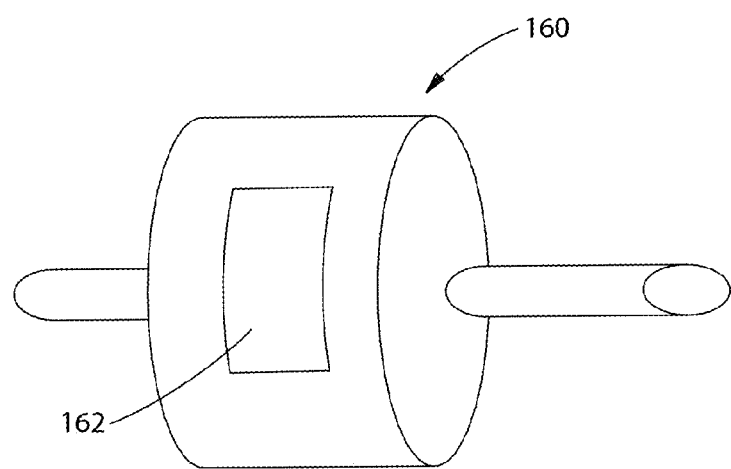
FIG. 28 shows one non-limiting example of a forming member for the step of forming the precursor web into an absorbent member wherein a portion of the absorbent member has been re-densified or compacted.

FIG. 28 shows one non-limiting example of a forming member 160 for the step of forming the precursor web 10 into an absorbent member with a density profile and different regions in the X-Y plane with different densities and/or different density profiles. As shown in FIG. 28, the forming member 160 comprises a roll having a region 162 thereon for compacting the de-densified absorbent material only in select areas/regions in the x-y plane. The region 162 on the roll 160 can be provided with any of the properties described above in conjunction with the preparation of a re-densified/compacted absorbent member.

Various alternative methods can be used to produce an absorbent member having X-Y regions with different densities and/or density profiles. Other alternative processes for producing such a structure include varying the depth of engagement (DOE), tooth geometry (TL, TD, TR), pitch, or number of hits for a specific region such that the region is more or less de-densified than the other regions of the absorbent member. Still other alternative methods for producing an absorbent member having X-Y regions with different densities and/or density profiles can involve de-densifying the precursor material using a combination of approaches, such as the de-densification step described in sections IA or B above, plus the "regional de-densification" process described in F2 below.

2. Absorbent Members with "Regional De-Densification.

The method of making an absorbent member with regional de-densification may be similar to the methods of de-densifying the precursor web such as described in sections IIA or B above. In order to make an absorbent member with regional de-densification, the precursor web is de-densified only in select areas/regions in the x-y plane. This can be done by providing selected portions of the forming structures which are free of forming elements such that they will leave portion(s) of the precursor web material in their original state. The portions of the forming structure which are free of forming elements can be substantially smooth. These portions of the forming structures can be arranged so that they align with one or more portions of the precursor web.

Figure 29:
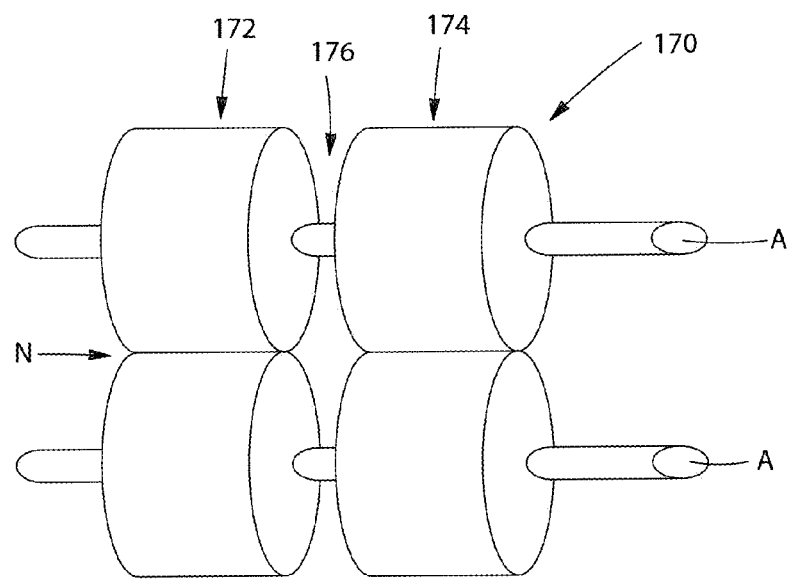
FIG. 29 shows one non-limiting example of a forming member for the step of forming the precursor web into an absorbent member with regional de-densification.

FIG. 29 shows one non-limiting example of a forming structure for the step of forming the precursor web into an absorbent member with regional de-densification. As shown in FIG. 29, the forming structure 170 comprises two spaced apart pairs 172 and 174 of counter-rotating rolls that rotate on the same axes. The rolls may comprise any of the types of rolls described herein for de-densifying the precursor web. When the precursor web is fed into the nip N between the pairs of rolls 172 and 174, the portions of the precursor web (such as along the longitudinal side regions of the web) contacted by the rolls 172 and 174 will be de-densified, while the central region of the web the is in the gap 176 between the rolls is not. In other embodiments, the arrangement of the forming structure shown in FIG. 29 can be varied to de-densify any suitable region(s) of the precursor web.

G. Alternative Embodiments and Combinations

The methods described herein may be used for a variety of purposes. Such purposes can range from serving as a pre-processing step prior to feeding the precursor material into a hammer mill in order to reduce the energy required to defibrillate the material in the hammer mill, to serving as a unit operation in an absorbent article manufacturing line in order to prepare a completed absorbent member that is ready for use in an absorbent article being made on the line.

Numerous alternative embodiments and combinations of the foregoing methods are possible. For instance, a precursor web can be fed through the apparatuses described herein any number of times, and the web can be thereafter fed through another one of the apparatuses any number of times. In addition, as shown in FIGS. 12 and 13, more than one absorbent member can be combined to form still other absorbent structures, and these absorbent structures can be fed together through any of the apparatuses described herein. In one non-limiting example, a precursor web can be fed through 20 passes of regional de-densification followed by five passes of all-over de-densification. The web can then be combined with a second de-densified layer and apertures can be formed in a region through both layers.

III. Examples

TABLE 1

Drylap Precursor Materials

| | 680 gsm Drylap | 300 gsm Drylap |
|---|---|---|
| Average Density (g/cc) | 0.51 | 0.44 |
| Location of Maximum (%) | 77 | 91 |
| Mean Maximum Density (g/cc) | 0.54 | 0.47 |
| Location of Minimum (%) | 95 | 7 |
| Mean Minimum Density (g/cc) | 0.49 | 0.42 |
| Ratio of Density Means Maximum/Minimum | 1.1 | 1.1 |
| Ratio of Density Means Maximum/Outer 5-15% | 1.1 | 1.1 |
| Ratio of Density Means Maximum/Outer 85-95% | 1.1 | 1.0 |
| Flexure-Resistance (N) | 81.0 | 28.1 |
| CD Peak Tensile (N) | 320.6 | 111.6 |
| MD Peak Tensile (N) | 395.1 | 175.7 |

Table 2 below shows the caliper increase of various drylap samples after 30 passes between nips formed between an 80 pitch staggered SELF roll and another 80 pitch staggered SELF of the type shown in FIGS. 16 and 17 at 0.000 inch (0 mm) depth of engagement and 50 feet per minute (15 meters/minute) line speed. When a number, such as "80" is given to describe the pitch, this refers to the number in thousands of an inch. The 80 pitch staggered SELF rolls have a diameter of 5.7 inch (14.5 cm), a uniform circumferential length dimension TL of about 0.080 inch (2 mm) measured generally from the leading edge LE to the trailing edge TE, a tooth tip radius TR at the tooth tip of about 0.005 inch (0.13 mm), are uniformly spaced from one another circumferentially by a distance TD of about 0.080 inch (2 mm), have a tooth height TH of about 0.138 inch (3.5 mm), have a tooth side wall angle of about 8.5 degrees, and a have a pitch of about 0.080 inch (2 mm). The SELF rolls are aligned in the CD such that the clearances on either side of the teeth are about equal. The clearance between the teeth of mating rolls linearly varies with the depth of engagement, ranging from a clearance 0.034 inch (0.86 mm) at −0.010 inch (0.25 mm) depth of engagement to a clearance of 0.029 inch (0.74 mm) at 0.015 inch (0.38 mm) depth of engagement. The rolls have a staggered tooth pattern and have square (vs. rounded) shape on the leading and trailing edges of the teeth, like that shown in FIG. 18.

TABLE 2

Increase in Caliper of Drylap Samples of Various Burst Strengths

|  | GP 4821 Treated | Tartas Bio Fluff TDR | GP 4825 Semi-treated | BoWater Coos Absorb SE | GP 4800 Untreated |
|---|---|---|---|---|---|
| Precursor Material Burst Strength (kPa) | 416 | 599 | 630 | 1143 | 1549 |
| Ave Base Caliper (mm; n = 3) | 1.50 | 1.80 | 1.50 | 1.72 | 1.40 |
| Ave Caliper Post SELFing (mm; n = 9) | 4.50 | 4.14 | 3.70 | 2.86 | 2.81 |
| Caliper Increase (mm) | 3.00 | 2.34 | 2.20 | 1.14 | 1.41 |

Table 3 below shows the properties of various drylap samples after 30 passes between nips formed between an 80 pitch staggered SELF roll and another 80 pitch staggered SELF roll of the type shown in FIGS. 16 and 17 at the specified depths of engagement (DOE) and a 50 feet per minute line speed. The same 80 pitch staggered SELF rolls used to produce the Examples in Table 2 (described above) are used.

TABLE 3

Two Side De-Densified Absorbent Members

|  | Ex. 1 | Ex. 2 | Ex. 3 | Ex. 4 | Ex. 5 | Ex. 6 | Ex. 7 | Ex. 8 | Ex. 9 |
|---|---|---|---|---|---|---|---|---|---|
| Target Material Basis Weight (gsm) | 300 | 300 | 500 | 400 | 400 | 680 | 680 | 300 | 300 |
| # Passes | 30 | 15 | 30 | 30 | 8 | 100 | 50 | 100 | 50 |
| DOE (inches/mm) | 0.010/0.25 | 0.010 | 0.005/0.127 | 0.007/0.18 | 0.007 | −0.005 | 0.005 | 0.005 | 0.015/0.38 |
| Average Density (g/cc) | 0.13 | 0.22 | 0.15 | 0.17 | 0.27 | 0.22 | 0.14 | 0.14 | 0.066 |
| Location of Maximum (%) | 49 | 44 | 54 | 58 | 63 | 52 | 58 | 48 | 47 |
| Mean Maximum Density (g/cc) | 0.22 | 0.31 | 0.25 | 0.30 | 0.38 | 0.38 | 0.24 | 0.21 | 0.010 |
| Location of Minimum (%) | 5 | 95 | 5 | 5 | 5 | 14 | 20 | 5 | 6 |
| Mean Minimum Density (g/cc) | 0.055 | 0.077 | 0.075 | 0.054 | 0.091 | 0.079 | 0.060 | 0.064 | 0.040 |
| Ratio of Density Means Maximum/Minimum | 4.0 | 4.0 | 3.3 | 5.5 | 4.2 | 4.8 | 4.0 | 3.3 | 2.5 |
| Ratio of Density Means Maximum/Outer 5-15% | 4.0 | 1.6 | 3.3 | 5.5 | 4.2 | 4.9 | 3.7 | 3.3 | 2.5 |
| Ratio of Density Means Maximum/Outer 85-95% | 2.8 | 4.0 | 2.5 | 2.2 | 1.9 | 4.1 | 2.0 | 2.0 | 1.8 |
| Flexure-Resistance (N) | 1.2 | 1.9 | 4.8 | 3.5 | 13.6 | 7.9 | 2.4 | 1.7 | 0.3 |
| MD Peak Tensile (N) | 6.6 | 13.9 | 20.0 | 11.9 | 44.6 | 19.2 | 2.9 | 3.8 | 0.4 |

Table 4 below shows the properties of various drylap samples after the specified number of passes between nips formed by rolls having the specified configurations and at the specified depths of engagement (DOE) and a 50 feet per minute line speed. All of the rolls used to produce the materials have similar diameters of about 5.7 inch. The same 80 pitch staggered SELF rolls used to produce the Examples in Table 2 (described above) are used. The anvil roll has a smooth surface. The 40 pitch ring roll has continuous ridges and grooves similar to the top roll (roll 142) shown in FIG. 27. The 40 pitch ring roll has a tooth height TH of about 0.080 inch and a tooth tip radius TR at the tooth tip of about 0.004 inch. The 80 pitch staggered SELF roll is aligned with the 40 pitch ring roll such that there are two ring roll teeth in-between each row of SELF teeth. The 80 pitch staggered SELF roll and 40 pitch ring roll are aligned in the CD such that the clearances on either side of the SELF teeth on the 80 pitch roll are about equal.

TABLE 4

One Side De-Densified Absorbent Members

|  | Example 10 | Example 11 | Example 12 | Example 13 |
|---|---|---|---|---|
| Target Precursor Material Basis Weight (gsm) | 300 | 300 | 500 | 400 |

TABLE 4-continued

One Side De-Densified Absorbent Members

| | Example 10 | Example 11 | Example 12 | Example 13 |
|---|---|---|---|---|
| Tooling Configuration | 80 pitch Staggered SELF against Smooth Anvil | 80 pitch Staggered SELF against 40 pitch Ring Roll | 80 pitch Staggered SELF against 40 pitch Ring Roll | 80 pitch Staggered SELF against 40 pitch Ring Roll |
| # Passes | 30 | 30 | 30 | 28 |
| DOE (inches/mm) | −0.003/−0.076 | 0.003/0.076 | −0.010/−0.25 | 0.000 |
| Average Density (g/cc) | 0.42 | 0.15 | 0.46 | 0.26 |
| Location of Maximum (%) | 85 | 80 | 64 | 75 |
| Mean Maximum Density (g/cc) | 0.58 | 0.22 | 0.61 | 0.49 |
| Location of Minimum (%) | 5 | 5 | 5 | 5 |
| Mean Minimum Density (g/cc) | 0.16 | 0.077 | 0.15 | 0.078 |
| Ratio of Density Means Maximum/Minimum | 3.5 | 2.9 | 4.0 | 6.3 |
| Ratio of Density Means Maximum/Outer 5-15% | 3.5 | 2.9 | 4.0 | 6.3 |
| Ratio of Density Means Maximum/Outer 85-95% | 1.0 | 1.5 | 1.2 | 1.7 |
| Flexure-Resistance (N) | 5.3 | 1.2 | 18.9 | 5.9 |
| MD Peak Tensile (N) | 70.5 | 7.8 | 122.0 | 28.0 |

Figure 30:
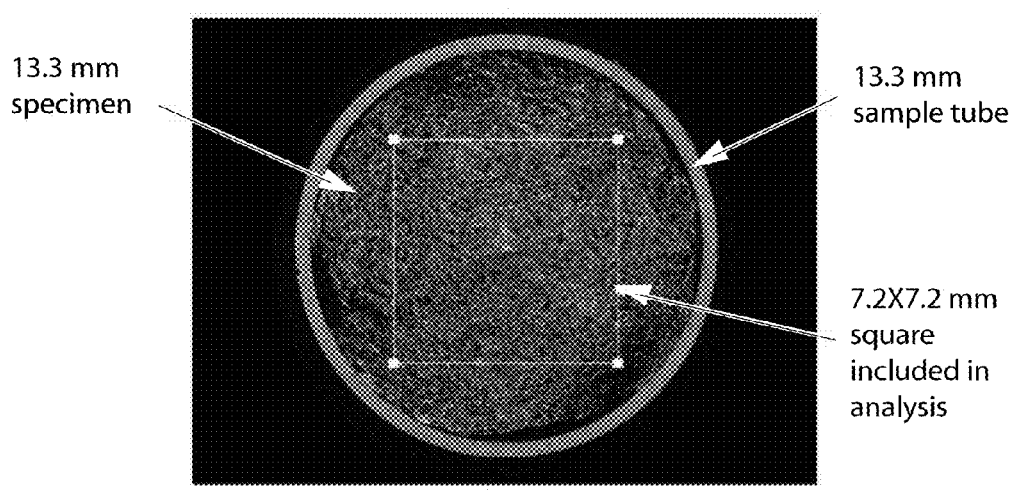
FIG. 30 is a schematic top view showing the specimen for the micro CT test method.
Figure 31:
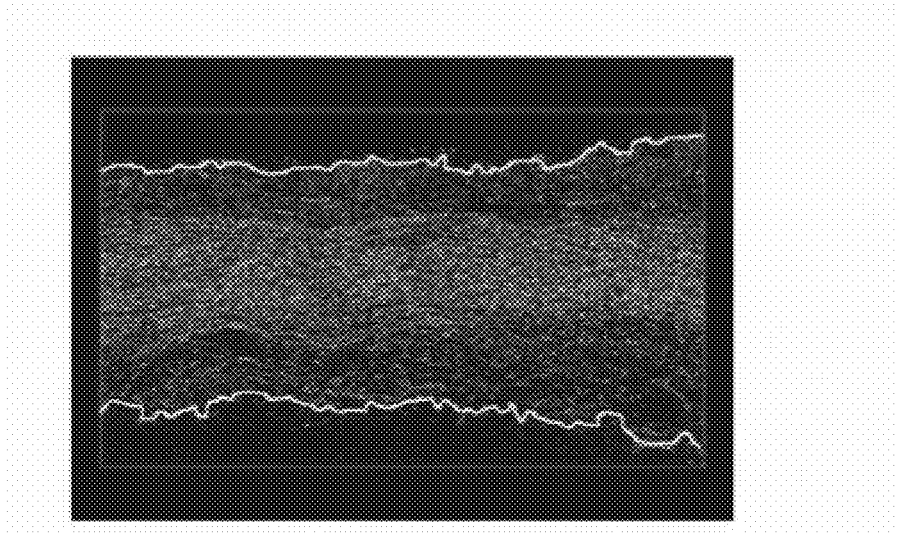
FIG. 31 is a schematic side view of the region of interest (ROI) of a specimen analyzed by the micro CT test method.

Table 5 shows the difference in caliper and flexibility of a compacted two-side de-densified structure relative to an uncompacted two-side de-densified structure. The compacted structure is thinner than the uncompacted structure, while maintaining similar flexibility. Example 14 is produced by passing samples of 500 gsm drylap through a nip formed between an 80 pitch staggered SELF roll and another 80 pitch staggered SELF of the type shown in FIGS. 16 and 17, 30 times, at 0.005 inch depth of engagement and a 50 feet per minute line speed. The same 80 pitch staggered SELF rolls used to produce the Examples in Table 2 (described above) are used. Example 15 is de-densified in the same manner as Example 14, then compacted all over using a flat metal plate and a die press.

TABLE 5

Compacted Absorbent Structures

| | Target Basis Weight (gsm) | Mechanical Treatment | Average Caliper (mm) | Average Flexibility (N) |
|---|---|---|---|---|
| Example 14 | 500 | 30 pass 80 pitch SELF on SELF at 0.005 inch (0.127 mm) DOE (no compaction) | 3.25 | 4.8 |
| Example 15 | 500 | 30 pass 80 pitch SELF on SELF at 0.005 inch DOE, then compacted | 2.20 | 5.5 |

Table 6 shows an example in which a de-densified and compacted absorbent member is thinner and more flexible than an absorbent member with processed with fewer passes. Example 16 is produced using the same tooling and settings as Example 14 above, but with only 17 passes through the nip. Example 17 is produced in the exact same manner as Example 15 above.

TABLE 6

Compaction versus Fewer Passes

| Option | Precursor Material Target Basis Weight (gsm) | Mechanical Treatment | Average Caliper (mm) | Average Flexibility (N) |
|---|---|---|---|---|
| Example 16 | 500 | 17 pass 80 pitch SELF on SELF at 0.005 inch DOE | 2.47 | 11.5 |
| Example 17 | 500 | 30 pass 80 pitch SELF on SELF at 0.005 inch DOE, then compacted | 2.20 | 5.5 |

IV. Test Methods

A. MicroCT Analysis of Absorbent Members for Density Determination

Micro-computed tomography (mCT) is used to quantitatively measure the density profile throughout the thickness of the absorbent member non-invasively.

Scanning Protocol

A disposable absorbent article is removed from its packaging and laid flat, taking care to not disturb the absorbent member material. Specimen discs 13.3 mm in diameter are cut from the center of the area to be tested in the disposable absorbent article through its entire thickness using curved tip scissors. The specimen is preferably chosen in an area that is free of embossments and apertures. The portion of the specimen to be analyzed should only include the unitary absorbent member as defined by the specification. The portion of the specimen to be analyzed can be physically removed from the specimen prior to scanning if it can be done in a way that does not disrupt the thickness or density of the portion of the specimen to be analyzed. Otherwise, the entire specimen is scanned and any additional material that is not part of the portion of the specimen to be analyzed should be digitally removed from the slices through cropping in step 2 below.

The specimen or portion of the specimen, herein after referred to as sample, is imaged using a micro-computed tomography system (µCT 40, ID#4286, Scanco Medical AG) or equivalent instrument. A custom short sample tube of length 30 mm and internal diameter 13.3 mm is used to position the sample for scanning. A 2 mm thick spacer of suitable material with low x-ray attenuation (e.g. polystyrene foam) is used to prop the sample off of the bottom of sample tube to avoid any attenuation interference from the plastic tube bottom. The sample is mounted horizontally with the top side of sample exposed to air with no contact from other materials. Image acquisition parameters of the 3-D isotropic scan are high resolution (1000 projections) with the x-ray tube set for a current of 180 µA and a peak energy of 35 kVp, with a 300 millisecond integration time and frame averaging set at 10. Horizontal slices are acquired with a slice increment of 8 µm throughout the thickness of the sample. Each slice consisting of 2000 projections (1000 projections/180 degrees) is used to reconstruct the CT image in a 2048×2048 pixel matrix, with a pixel resolution of 8 µm. To eliminate any edge effects, only the central 7.2 mm×7.2 mm square area of each slice is used for subsequent analysis.

Image Analysis

If the portion of the unitary absorbent member is physically removed from the specimen prior to insertion into the sample tube, then the central 7.2×7.2 mm square portion of the unitary absorbent member in the sample tube is subjected to image analysis as described below. If the entire specimen is inserted in to the sample tube, then only the central 7.2×7.2 mm square portion of the unitary absorbent portion of the specimen is subjected to the image analysis described below. In either case, the central 7.2×7.2 mm square portion will be referred to herein as the portion of interest or POI.

The objective of the image analysis is to quantitatively measure the density distribution through the thickness of the POI and verify the uniformity of the POI using the following outputs:

Density distribution through the thickness of the POI (used to quantify the density profile of the POI)

Average thickness for the entire POI and the 4 quadrants of the POI (used in the acceptance criterion to verify sample uniformity described below)

Acceptance Criteria: In order for a POI to be acceptable, it must have a uniform thickness (i.e. the average thickness of each quadrant within the POI must be within 50% of the average thickness of the entire POI), as defined in step 12 below.

Image Analysis Procedure: After collection of 3-D MicroCT data in an ISQ file (the proprietary format for Scanco Medical microCT scanner), the data are transferred to a Mac Pro workstation running RedHat 4 Linux, or equivalent computer system. Data analysis is performed using Matlab 7.6.0.324 and Avizo 6.1 or equivalent software. The following steps are applied to the 3-D data set:

1. The ISQ file is converted from 16 bit to 8 bit stack of TIFF images using a scaling factor of 0.05 and an offset of 0. Each image within the stack is cropped such that only the central 7.2 mm×7.2 mm square portion of the image remains.
2. Each stack of TIFF images from Step 1 is then examined using AVIZO (VSG, Burlington, Mass.), a high end 3-D visualization software application. Any noise or artifacts not desired in the measured data set are removed using the VolumeEdit feature in AVIZO. Note: The editing step ensures that the data associated with the POI will be accurate and extraneous data are removed. This editing step must be done carefully or it can lead to incorrect identification of the POI. Any additional material used to secure the sample or not part of the POI should be digitally removed from the slices through cropping out those extraneous regions so they are not included in the analysis.
3. The cleaned data are then saved in AVIZO as a 3-D avw file.
4. The 3-D sample created in Step 3 is divided into four quadrants. Each quadrant has the same Z dimension as the original sample, but the X/Y dimensions are divided by 2. For example a sample that was originally of dimensions 1000×1000×500 (X by Y by Z) pixels would be broken into four quadrants each with dimensions of 500×500×500 pixels. Each quadrant, as well the original data set is analyzed in an identical manner as described in the steps below.
5. A threshold is chosen to separate the fibers from the background. This is chosen using an automated method in Matlab (Otso's method). The same threshold should then be used for all subsequent scans of absorbent members of like material. Note: Correct thresholding is an important variable to determine a correct POI. A visual inspection should be performed as a check to determine that this threshold seems optimal for the fiber type.
6. Depth maps of top and bottom surfaces are then created. A depth map is a 2-D image where the grey level value represents the distance from the top of the POI to the surface of the layer.
7. These depth images are then median filtered using 5 iterations of an 11×11 median filter to remove spurious fibers. These depth images are then converted back to coordinates in 3-D space and serve as the top and bottom surfaces of the absorbent member.
   Note: Increased/Decreased median filtering will allow more of the fibers to be included and will make the POI larger. The amount of median filtering should not change within a study and the resulting POI should be inspected visually after analysis.
8. The thickness of the POI is calculated by subtracting the top and bottom depth maps. An average of the non-zero values of this subtraction provides the average thickness of the POI.
9. Starting from the top surface the density is normalized to 0-100%, where the percentages represent the Z-direction location throughout the thickness of the web (0%—top surface, 100%—bottom surface). At each percentage point in-between the grey level value is recorded. This is repeated for all points in the POI.
10. The absorbent member data are converted to a 3-D Volume that has the same X/Y dimensions as the original data, but the Z dimension is now 100, reflecting the percentage through the sample.
11. A histogram is created of the mean of all the grey levels at 1%, 2%, 3%, ... 100%. A .csv file is created and sent to Excel.
12. In order to determine if the thickness of the POI is uniform, the average thickness of each the 4 quadrants, which is determined in step 8, should be verified to be within 50% of the average thickness determined for the overall POI. If one or more quadrants are 50% different, then a new specimen is selected and analyzed.

Calibration of Density

In order to calibrate the relationship between the output grey level data from Step 11 to relevant density values, a small calibration study is performed using standard foams with known densities. The density of the calibration samples is determined by die cutting a cube and measuring the length (L), width (W) and height (H) of the sample using the caliper method defined below, measuring the weight of the sample to the nearest 0.01 g using a calibrated balance, then dividing the weight of the sample by the volume (L×W×H). The known density values of the calibration samples are then correlated with the average grey level values after measurement of the calibration samples by MicroCT using the same scanning parameters as those used in this study.

Six calibration samples of homogeneous, commercially available, non-metallic foams, each having a different density and made of a polymeric material, are measured by the same protocol as described above. The calibration samples and the test specimens consist essentially of elements selected from carbon, hydrogen, oxygen and nitrogen atoms, and combinations thereof. The foam samples are chosen so that the average density of the POI analyzed above lies between that of the least dense and most dense foam calibration samples. For each foam sample, the average grey value is determined from the center of the foam sample. i.e. 45% to 55%. This value is then plotted against the known density of each foam sample. This produces a set of points to which a least-squares regression is fitted (either linear or nonlinear). However, the correlation coefficient $r^2$ should be at least >0.90 for the linear regression. For $r^2$ values less than 0.90, the calibration should be re-done with different foam samples if necessary. The equation describing the regression is then used to convert the grey level values of the MicroCT data to density values measured in g/cc.

Calculations
1. The mean grey levels created in step 11 are converted to density values for each z-direction location (i.e. 5%, 6%, 7%, . . . 95%) using the calibration curve generated from the regression described above.
2. To calculate the average density, the density values from 5-95% are averaged.
3. To calculate the mean outer 5-15% density, the density values from 5-15% are averaged.
4. To calculate the mean outer 85-95% density, the density values from 85-95% are averaged.
5. To calculate the mean maximum density, the maximum density from 5-95% is located and the average density is calculated using the data points ranging from (maximum −5%) to (maximum +5%). For example, if the maximum is located at 45%, the mean peak density is calculated using the density values from 40-50%. If the maximum density falls at a location that is ≤10% through the thickness of the sample, then the mean outer 5-15% density calculation is used. If the maximum density falls at a location that is ≥90% through the thickness of the sample, then the mean outer 85-95% density calculation is used.
6. To calculate the mean minimum density, the minimum density from 5-95% is located and the average density is calculated using the data points ranging from (minimum −5%) to (minimum +5%). For example, if the minimum was located at 15%, the mean peak density is calculated using the density values from 10-20%. If the minimum density falls at a location that is ≤10% through the thickness of the sample, then the mean outer 5-15% density calculation is used. If the minimum density falls at a location that is ≥90% through the thickness of the sample, then the mean outer 85-95% density calculation is used.
7. To calculate the ratio of the mean maximum density to the mean minimum density, the mean maximum density is divided by the mean minimum density.
8. To calculate the ratio of the mean maximum density to the mean outer 5-15% density, the mean maximum density is divided by the mean outer 5-15% density.
9. To calculate the ratio of the mean maximum density to the mean outer 85-95% density, the mean maximum density is divided by the mean outer 85-95% density.

B. Flexibility Method

The flexibility of the absorbent member is quantified by measuring the peak bending stiffness, or flexure-resistance, following the CIRCULAR BEND PROCEDURE. The lower the value, the lower the flexure-resistance, and the higher the flexibility of the sample.

Apparatus

The apparatus necessary for the CIRCULAR BEND PROCEDURE is a modified Circular Bend Stiffness Tester, having the following parts:
1. A smooth-polished steel plate platform which is 102.0× 102.0×6.35 millimeters having an 18.75 millimeter diameter orifice centered within the plate. The lap edge of the orifice should be at a 45 degree angle to a depth of 4.75 millimeters.
2. A plunger having an overall length of 72.2 millimeters, a diameter of 6.25 millimeters, a ball nose having a radius of 2.97 millimeters and a needle-point extending 0.88 millimeter therefrom having a 0.33 millimeter base diameter and a point having a radius of less than 0.5 millimeter, the plunger being mounted concentric with the orifice and having equal clearance on all sides. The bottom of the plunger should be set well above the top of the orifice plate. From this position, the downward stroke of the ball nose is to the exact bottom of the plate orifice.
3. A 100 N load cell (Model # SMT1-100N) or equivalent.
4. An actuator, and more specifically an MTS Synergie 400 (Model # SYN400), or equivalent.

Number and Preparation of Specimens

In order to perform the procedure for this test, as explained below, a minimum of four representative samples are necessary. Using a die cutter, a square 37.5×37.5 millimeter test specimen is cut from each sample. The specimen is cut from the center of the sample (e.g. centered on the intersection of the longitudinal and transverse centerlines). The portion of the specimen to be tested should only include the unitary absorbent member as defined by the specification. Therefore, the other materials that are not part of the absorbent member must be carefully removed, and test specimens should not be folded or bent by the test person to avoid affecting flexural-resistance properties.

Procedure

The procedure for the CIRCULAR BEND PROCEDURE is as follows. The test plate is leveled. The plunger speed is set at 50.0 centimeters per minute per full stroke length. A specimen is centered on the orifice platform below the plunger such that the body surface of the specimen is facing the plunger and the garment surface of the specimen is facing the platform. The indicator zero is checked and adjusted, if necessary. The plunger is actuated. Touching the specimen during the testing should be avoided. The maximum force reading to the nearest 0.1 N is recorded. The above steps are repeated until all four of the specimens have been tested.

Calculations

The peak bending stiffness, or flexure-resistance, for each specimen is the maximum force reading for that specimen.

Each specimen is measured individually and the average of the samples is reported to the nearest 0.1 N.

C. Caliper Method

Apparatus

The caliper of the material is quantified using a Thwing-Albert ProGage Thickness Tester or equivalent with a 56.4 millimeter diameter circular foot.

Number and Preparation of Specimens

A minimum of 3 representative samples are necessary to complete the testing. One specimen is cut from each of the 3 samples for a total of 3 test specimens. The specimen is cut from the center of the sample (e.g. centered on the intersection of the longitudinal and transverse centerlines). The portion of the specimen to be tested should only include the unitary absorbent member as defined by the specification. Therefore, the other materials that are not part of the absorbent member must be carefully removed such that the caliper of the material is not impacted. The specimens to be measured must be ≥65 millimeters in diameter to ensure the entire surface area of the foot comes in contact with the sample being measured. The highlighted text obviously does not apply to the calibration foam materials for which this method is used.

Procedure

The test apparatus is always zeroed before any measurements are taken. The foot starts 0.5 inches above the surface on which the test specimen is placed and descends at a rate of 0.125 inches per second. When the foot reaches the target pressure of 0.51 kilopascals, it remains in contact with the specimen for 9 seconds while maintaining that pressure. The reading is taken at the end of the 9 second period.

Calculations

Each of the samples is individually measured and the average of the samples is reported to the nearest 0.01 millimeters.

D. Tensile Method

The MD and CD peak tensile are measured using a method based on Standard Test WSP 110.4 (05)—Option B, Standard Test Method for Breaking Force and Elongation of Nonwoven Materials (Strip Method), but with a shorter gauge length to enable measurements on finished products.

Apparatus

The apparatus necessary for the TENSILE METHOD consists of the following parts: 1) An MTS Synergie 400 (Model # SYN400) or equivalent with a constant-rate-of-extension of 100 mm/min; 2) A 100 N load cell (Model # SYN100) or equivalent, or a 500N load cell (Model # SYN 500) or equivalent for stiffer materials such as undeformed drylap.

Number and Preparation of Specimens

A minimum of eight representative samples are necessary, four for the MD tensile test and four for the CD tensile test. The specimen is cut from the center of the sample (e.g. centered on the intersection of the longitudinal and transverse centerlines). The portion of the specimen to be tested should only include the unitary absorbent member as defined by the specification. Therefore, the other materials that are not part of the absorbent member must be carefully removed such that the tensile strength of the material is not impacted. To prepare the samples for the MD tensile test, a specimen is die cut from each sample with a CD width of 50 mm and a MD length of 70 mm. For a sample that is being taken from a product, such as a feminine pad, the MD is assumed to represent the long direction of the pad and the CD is the direction orthogonal to the MD. To prepare the samples for the CD tensile test, a specimen is die cut from each sample with a MD length of 50 mm and a CD width of 50 mm Procedure Standard Test WSP 110.4 (05)—Option B is followed with the following gauge length changes:
1. MD peak tensile: 50 mm gauge length
2. CD peak tensile: 30 mm gauge length Calculations The peak tensile is the maximum force reading for that specimen. Each specimen is measured individually and the average peak MD tensile and average peak CD tensile of the samples is reported to the nearest 0.1 N.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 grams" is intended to mean "about 40 grams".

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for making an absorbent member having a thickness, said method comprising:
   a) providing a precursor web material, said precursor web material comprising a wetlaid cellulosic fibrous structure, said precursor web material having a first surface, a second surface, and a thickness;
   b) providing a pair of forming members having a machine direction orientation and a cross-machine direction orientation, said forming members comprising:
      a first forming member having a surface comprising a plurality of first forming elements, wherein said first forming elements comprise discrete male forming elements that are spaced apart in the machine direction; and
      a second forming member having a surface comprising a plurality of second forming elements, wherein said second forming elements comprise male forming elements;
   c) providing a third forming member having a machine direction orientation and a cross-machine direction orientation, said third forming member having a surface comprising a plurality of third forming elements, wherein said third forming elements comprise discrete male forming elements that are spaced apart in the machine direction;

d) mechanically impacting said precursor web material by placing said precursor web material between said first and second forming members, wherein said forming elements on said first forming member penetrate into the first surface of said precursor web material at least part of the way into the thickness of said precursor web material, and said forming elements on said second forming member penetrate into the second surface of said precursor web material at least part of the way into the thickness of said precursor web material; and e) repeating a step of mechanically impacting said precursor web to form an absorbent member by mechanically impacting said precursor web material by placing said precursor web material between said third forming member and either the first forming member, the second forming member or another forming member, wherein said forming elements on said third forming member penetrate into the first or second surface of said precursor web material at least part of the way into the thickness of said precursor web material, wherein the only material that is mechanically impacted in steps d) and e) consists of wetlaid cellulosic fibrous material, wherein said absorbent member is provided with a density profile through at least a portion of its thickness, and wherein said first and second surfaces of said precursor web material comprise first and second surfaces, respectively, of said absorbent member, and said first and second surfaces of said absorbent member are substantially planar and not substantially embossed.

2. The method of claim 1 wherein the precursor web material is selected from the group consisting of: drylap, liner board, paper board, post-consumer recycled material, filter paper, and combinations thereof.

3. The method of claim 2 wherein the precursor material consists of treated drylap.

4. The method of claim 1 wherein the precursor web has an initial density prior to mechanically impacting the same, and the absorbent member formed by the method has a mean maximum density, and the mean maximum density of the absorbent member is less than the initial density of the precursor web.

5. The method of claim 1 wherein the precursor web material has a burst strength of less than about 1,000 kPa.

6. The method of claim 1 wherein the precursor web is treated with debonders.

7. The method of claim 1 wherein said pair of forming members define a clearance which is the shortest distance between the forming elements on one forming member and the forming elements on the opposed forming member, and the clearance between the forming elements is less than the thickness of the precursor web.

8. The method of claim 1 wherein said pair of forming members define a depth of engagement, and the ratio of the thickness of the precursor web to the absolute value of the depth of engagement is greater than 1.

9. The method of claim 1 wherein said pair of forming members comprise counter-rotating rolls defining a nip therebetween.

10. The method of claim 9 wherein said counter-rotating rolls rotate at substantially the same surface speed.

11. The method of claim 9 wherein said counter-rotating rolls rotate at different surface speeds, and the surface speed differential between said rolls is greater than about 0.3%.

12. The method of claim 9 wherein the first forming member comprises a first roll, and the second forming member comprises a second roll, and at least said first roll comprises a plurality of alternating discrete ridges and grooves on its surface, wherein the ridges have breaks therein to provide forming elements in the form of teeth.

13. The method of claim 12 wherein said teeth have a tip radius that is less than about 0.02 inch (0.5 mm).

14. The method of claim 1 wherein at least one of said first and second forming members has at least one relatively smooth region on its surface.

15. The method of claim 9 comprising inserting said web material through multiple nips wherein said multiple nips are formed by plural rolls arranged in a paired configuration.

16. The method of claim 9 comprising inserting said web material through multiple nips wherein said multiple nips are formed by plural rolls arranged in a nested configuration in which there are at least four rolls and at least two of the rolls define two or more nips with the other rolls.

17. The method of claim 9 comprising inserting said web material through multiple nips wherein said multiple nips are formed by plural rolls arranged in a combination of nested and paired configurations, wherein in the nested configuration there are at least four rolls and at least two of the rolls define two or more nips with the other rolls.

18. The method of claim 1 wherein the forming elements on said forming members only penetrate part of the way through the thickness of said precursor web material.

19. The method of claim 1 wherein the forming elements on at least one of said forming members penetrate completely through the thickness of said precursor web material.

20. The method of claim 1 further comprising a step of feeding said absorbent member into a hammer mill.

21. A method of making an absorbent article on an absorbent article manufacturing line wherein the method of claim 1 is carried out on said absorbent article manufacturing line.

22. The method of claim 9 wherein said nip comprises a first nip, and said method further comprises a subsequent step of passing said web material through at least one additional nip between two additional rolls after said web material is inserted through said first nip, said additional rolls having surfaces that form said additional nip, wherein at least regions of the surfaces of at least one of said additional rolls are relatively smoother in at least a portion of said additional nip in comparison to the surfaces of the rolls in said first nip, wherein said additional nip compacts at least a portion of said precursor web material.

23. The method of claim 9 wherein the first forming elements have a spacing therebetween and the second forming elements have a spacing therebetween, said method further comprising a prior and/or subsequent step of passing said web material through at least one additional nip between two additional rolls, said additional rolls having forming elements thereon which have a spacing therebetween that is greater than the spacing between the first forming elements and the second forming elements, said additional rolls having a depth of engagement greater than 0.04 inches, wherein said forming elements on said additional rolls form a plurality of protrusions in said web material.

24. The method of claim 9 further comprising a prior and/or subsequent step of passing said web material through at least one additional nip between two additional rolls, wherein at least one of said additional rolls has elements on its surface that penetrate the thickness of said web material to form apertures in said web material.

25. A method of reducing the defibrization energy of wet laid pulp, said method comprising:
   a) providing a precursor web material, said precursor web material comprising a wetlaid cellulosic fibrous structure, said precursor web material having a first surface, a second surface, and a thickness;
   b) providing a pair of forming members having a machine direction orientation and a cross-machine direction orientation, said forming members comprising:
      a first forming member having a surface comprising a plurality of first forming elements, wherein said first forming elements comprise discrete male forming elements that are spaced apart in the machine direction; and
      a second forming member having a surface comprising a plurality of second forming elements, wherein said second forming elements comprise male forming elements;
   c) providing a third forming member having a machine direction orientation and a cross-machine direction orientation, said third forming member having a surface comprising a plurality of third forming elements, wherein said third forming elements comprise discrete male forming elements that are spaced apart in the machine direction;
   d) mechanically impacting said precursor web material by placing said precursor web material between said first and second forming members, wherein said forming elements on said first forming member penetrate into the first surface of said precursor web material at least part of the way into the thickness of said precursor web material, and said forming elements on said second forming member penetrate into the second surface of said precursor web material at least part of the way into the thickness of said precursor web material; and
   e) repeating a step of mechanically impacting said precursor web by mechanically impacting said precursor web material by placing said precursor web material between said third forming member and either the first forming member, the second forming member or another forming member, wherein said forming elements on said third forming member penetrate into the first or second surface of said precursor web material at least part of the way into the thickness of said precursor web material, wherein the only material that is mechanically impacted in steps d) and e) consists of wetlaid cellulosic fibrous material,
   wherein said absorbent member is provided with a density profile through at least a portion of its thickness, and
   wherein said first and second surfaces of said precursor web material comprise first and second surfaces, respectively, of said absorbent member, and said first and second surfaces of said absorbent member are substantially planar and not substantially embossed.

26. The method of claim 1 wherein said discrete male forming elements on said first forming member comprise teeth having a length ranging from about 0.5 mm to about 10 mm.

27. The method of claim 1 wherein said discrete male forming elements on said first forming member comprise teeth having a spacing therebetween ranging from about 0.5 mm to about 10 mm.

28. The method of claim 1 wherein said precursor web material comprises at least about 90 weight percent cellulose fibers.

29. The method of claim 1 wherein said precursor web material has a density of between about 0.25 g/cc and about 0.6 g/cc.

30. The method of claim 3 wherein said precursor web material has a density of between about 0.25 g/cc and about 0.6 g/cc.

31. The method of claim 3 wherein the precursor material comprises dry lap that has a basis weight in a range from about 200 gsm to about 700 gsm.

32. The method of claim 1 wherein said discrete male forming elements have leading and trailing edges, and said precursor web material is bent around the leading and trailing edges of the discrete male forming elements during step (d).

33. The method of claim 1 wherein a direction into the thickness of the absorbent member is designated as the z-direction, and said absorbent member is provided with a density profile through its thickness, wherein the zone of said absorbent member with the highest density is located generally in the middle of the absorbent member in the z-direction, and the zones of the absorbent member with the lowest densities are located generally adjacent to the surfaces of the absorbent member, which surfaces correspond to the first and second surfaces of the precursor web material.

34. A method for making an absorbent member having a thickness, said method comprising:
   a) providing a precursor web material, said precursor web material comprising a wetlaid cellulosic fibrous structure having a density of between about 0.25 g/cc and about 0.6 g/cc, said precursor web material having a first surface, a second surface, and a thickness;
   b) providing a pair of forming members comprising counter-rotating rolls defining a nip therebetween, said rolls having a machine direction orientation and a cross-machine direction orientation, said rolls comprising:
      a first roll having a first surface and a first axis about which said first roll rotates, wherein said first roll comprises a plurality of ridges and grooves, wherein said ridges comprise discrete teeth that are spaced apart in the machine direction; and
      a second roll having a second surface and a second axis about which said second roll rotates, wherein said second roll comprises a plurality of ridges and grooves, wherein said ridges on said second roll also comprise a discrete teeth that are spaced apart in the machine direction, wherein the teeth on said first roll are aligned in between the grooves on said second roll;
   c) providing a third forming member comprising a third roll having a machine direction orientation and a cross-machine direction orientation, said third roll having a surface comprising a plurality of third forming elements, wherein said third forming elements comprise discrete male forming elements that are spaced apart in the machine direction;
   d) mechanically impacting said precursor web material by moving said web material through the nip between said first and second counter-rotating rolls, wherein said teeth on said first roll penetrate into the first surface of said precursor web material, and said teeth on said second roll penetrate into the second surface of said precursor web material; and
   e) repeating a step of mechanically impacting said precursor web to form an absorbent member by mechanically impacting said precursor web material by moving said precursor web material through a nip between said third roll and either the first roll, the second roll or another roll, wherein said forming elements on said third roll penetrate into the first or second surface of said precursor web material at least part of the way into the thickness of said precursor web material, wherein said absorbent member is provided with a density profile through at least a portion of its thickness, wherein the only material that is mechanically impacted in steps d) and e) consists of wetlaid cellulosic fibrous material, and wherein said first and second surfaces of said precursor web material comprise first and second surfaces, respectively, of said absorbent member, and said first and second surfaces of said absorbent member are substantially planar and not substantially embossed.

35. The method of claim 34 wherein the ridges on the first and second rolls are oriented perpendicular to the first axis and second axis, respectively.

36. The method of claim 34 wherein the ridges on the first and second rolls are oriented parallel to the first axis and second axis, respectively.

37. The method of claim 1 wherein said absorbent member is substantially free of binder material.

38. The method of claim 1 wherein said absorbent member is completely free of binder material.

39. A method for making an absorbent member having a thickness, said method comprising:
  a) providing a precursor web material, said precursor web material comprising a wetlaid cellulosic fibrous structure, said precursor web material having a first surface, a second surface, and a thickness;
  b) providing a pair of forming members having a machine direction orientation and a cross-machine direction orientation, said forming members comprising:
    a first forming member having a surface comprising a plurality of first forming elements, wherein said first forming elements comprise discrete male forming elements that are spaced apart in the machine direction; and
    a second forming member having a surface comprising a plurality of second forming elements, wherein said second forming elements comprise male forming elements;
  c) providing a third forming member having a machine direction orientation and a cross-machine direction orientation, said third forming member having a surface comprising a plurality of third forming elements, wherein said third forming elements comprise discrete male forming elements that are spaced apart in the machine direction;
  d) mechanically impacting said precursor web material by placing said precursor web material between said first and second forming members, wherein said forming elements on said first forming member contact the first surface of said precursor web material and portions of said precursor web material bend around the forming elements on the first forming member, and said forming elements on said second forming member contact the second surface of said precursor web material and portions of said precursor web material bend around the forming elements on the second forming member; and
  e) repeating a step of mechanically impacting said precursor web to form an absorbent member by mechanically impacting said precursor web material by placing said precursor web material between said third forming member and either the first forming member, the second forming member or another forming member, wherein portions of said precursor web material on the first or second surface of said precursor web material bend around said forming elements on said third forming member, wherein the only material that is mechanically impacted in steps d) and e) consists of wetlaid cellulosic fibrous material, wherein said absorbent member is provided with a density profile through at least a portion of its thickness, and wherein said first and second surfaces of said precursor web material comprise first and second surfaces, respectively, of said absorbent member, and said first and second surfaces of said absorbent member are substantially planar and not substantially embossed.

* * * * *